(12) United States Patent
Quan et al.

(10) Patent No.: US 12,324,663 B2
(45) Date of Patent: Jun. 10, 2025

(54) SYSTEMS AND METHODS FOR MAKING AND USING SENSORS, PROBES, AND OTHER DEVICES

(71) Applicant: President and Fellows of Harvard College, Cambridge, MA (US)

(72) Inventors: Qimin Quan, Somerville, MA (US); Wooyoung Hong, Gyeonggi-do (KR); Marko Loncar, Belmont, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 308 days.

(21) Appl. No.: 15/310,253

(22) PCT Filed: May 11, 2015

(86) PCT No.: PCT/US2015/030125
§ 371 (c)(1),
(2) Date: Nov. 10, 2016

(87) PCT Pub. No.: WO2015/175398
PCT Pub. Date: Nov. 19, 2015

(65) Prior Publication Data
US 2017/0265788 A1    Sep. 21, 2017

Related U.S. Application Data

(60) Provisional application No. 61/991,842, filed on May 12, 2014.

(51) Int. Cl.
*A61B 5/1459* (2006.01)
*A61B 5/01* (2006.01)
(Continued)

(52) U.S. Cl.
CPC .............. *A61B 5/1459* (2013.01); *A61B 5/01* (2013.01); *A61B 5/05* (2013.01); *A61B 5/14546* (2013.01);
(Continued)

(58) Field of Classification Search
CPC ..... A61B 5/1459; A61B 5/14735; A61B 5/01; A61B 5/05; A61B 5/14556;
(Continued)

(56) References Cited

U.S. PATENT DOCUMENTS 3,779,628 A * 12/1973 Kapron ................ G02B 6/4203
                                                                385/43
5,457,041 A * 10/1995 Ginaven ........... A61M 37/0015
                                                                435/285.1
(Continued)

FOREIGN PATENT DOCUMENTS

CN    104487824 A    4/2015
CN    205679617 U    11/2016
(Continued)

OTHER PUBLICATIONS

Szunerits et al. (ChemComm., 2012, 48, 8999-9010) (Year: 2012).*
(Continued)

*Primary Examiner* — P. Kathryn Wright
*Assistant Examiner* — Curtis A Thompson
(74) *Attorney, Agent, or Firm* — Wolf, Greenfield & Sacks, P.C.

(57) ABSTRACT

The present invention generally relates, in some aspects, to systems and methods for making and using sensors or other devices, such as optical components. One aspect is generally directed to a sensor or other device comprising a nanometer-sized portion. In some embodiments, the sensor can be used to determine various characteristics such as temperature, humidity, an electric field, a magnetic field, an analyte, or the
(Continued)

like. For instance, in one embodiment, a portion of a sensor device may be inserted into a cell and used to study the cell, e.g., using optical techniques such as surface plasma resonance. In some embodiments, such sensors or other devices may comprise metal, glass, or other materials, which can be prepared using etching or other techniques.

25 Claims, 24 Drawing Sheets

(51) Int. Cl.
    *A61B 5/05*         (2021.01)
    *A61B 5/145*       (2006.01)
    *A61B 5/1455*      (2006.01)
    *A61B 5/1473*      (2006.01)
    *B82B 1/00*         (2006.01)
    *B82B 3/00*         (2006.01)
    *G01H 9/00*         (2006.01)
    *G01N 15/14*       (2024.01)
    *G01N 15/1429*     (2024.01)
    *G01N 15/1434*     (2024.01)
    *G01N 21/552*      (2014.01)
    *G01N 21/64*       (2006.01)
    *G01N 21/65*       (2006.01)
    *G01N 33/53*       (2006.01)
    *G01N 33/543*      (2006.01)
    *G01N 15/01*       (2024.01)
    *G01N 15/10*       (2006.01)

(52) U.S. Cl.
    CPC ...... *A61B 5/14556* (2013.01); *A61B 5/14735* (2013.01); *B82B 1/001* (2013.01); *B82B 3/0019* (2013.01); *G01H 9/00* (2013.01); *G01N 15/1429* (2013.01); *G01N 15/1434* (2013.01); *G01N 15/1484* (2013.01); *G01N 21/553* (2013.01); *G01N 21/6428* (2013.01); *G01N 21/65* (2013.01); *G01N 33/5308* (2013.01); *G01N 33/54373* (2013.01); *A61B 5/1455* (2013.01); *A61B 2562/0238* (2013.01); *A61B 2562/028* (2013.01); *A61B 2562/0285* (2013.01); *A61B 2562/029* (2013.01); *A61B 2562/125* (2013.01); *G01N 15/01* (2024.01); *G01N 2015/1006* (2013.01); *G01N 2201/08* (2013.01)

(58) Field of Classification Search
    CPC .......... A61B 5/14546; A61B 2562/029; A61B 2562/125; A61B 2562/028; A61B 2562/0285; A61B 2562/0238; A61B 5/1455; B82B 1/001; B82B 3/0019; G01N 33/5308; G01N 21/553; G01N 21/65; G01N 21/6428; G01N 33/54373; G01N 15/1429; G01N 15/1434; G01N 15/1484; G01N 2201/08; G01N 2015/0065; G01N 2015/1006; G01H 9/00
See application file for complete search history.

(56) References Cited

U.S. PATENT DOCUMENTS

| | | | |
|---|---|---|---|
| 6,645,757 B1* | 11/2003 | Okandan | C12M 35/02 204/403.01 |
| 2002/0028519 A1 | 3/2002 | Yguerabide et al. | |
| 2003/0112443 A1* | 6/2003 | Hjelme | G01N 21/7703 356/480 |
| 2003/0138819 A1 | 7/2003 | Gong et al. | |
| 2004/0012062 A1 | 1/2004 | Miyajima et al. | |
| 2004/0134884 A1 | 7/2004 | Wei et al. | |
| 2004/0182707 A1* | 9/2004 | Jardemark | G01N 33/5438 204/451 |
| 2005/0117157 A1* | 6/2005 | Tarsa | G01N 21/39 356/437 |
| 2005/0161594 A1* | 7/2005 | Hollingsworth | G02B 6/241 250/234 |
| 2007/0087436 A1* | 4/2007 | Miyawaki | B82Y 30/00 977/902 |
| 2007/0090836 A1 | 4/2007 | Xiang et al. | |
| 2007/0220882 A1* | 9/2007 | Culpepper | B81B 3/0062 60/527 |
| 2007/0256480 A1* | 11/2007 | Black | G01Q 70/14 73/105 |
| 2010/0124824 A1 | 5/2010 | Eilmsteiner et al. | |
| 2010/0297686 A1* | 11/2010 | Gogotsi | G01N 21/658 436/63 |
| 2011/0207237 A1* | 8/2011 | Sai | G01N 21/412 385/12 |
| 2011/0208031 A1* | 8/2011 | Wolfe | A61B 5/291 600/378 |
| 2011/0237445 A1 | 9/2011 | Svahn et al. | |
| 2011/0277249 A1 | 11/2011 | Abuzaina et al. | |
| 2012/0045748 A1 | 2/2012 | Willson et al. | |
| 2013/0137129 A1 | 5/2013 | Yu et al. | |
| 2013/0244895 A1 | 9/2013 | Voros et al. | |
| 2013/0286467 A1 | 10/2013 | Vlasko-Vlasov et al. | |
| 2013/0319123 A1* | 12/2013 | Wang | A61B 5/0095 73/655 |
| 2013/0338627 A1* | 12/2013 | Rylander | A61M 5/158 604/501 |
| 2014/0024131 A1 | 1/2014 | Kim et al. | |
| 2014/0218727 A1* | 8/2014 | Li | G01N 21/554 356/301 |
| 2014/0322729 A1 | 10/2014 | Fan et al. | |
| 2014/0334005 A1 | 11/2014 | Omenetto et al. | |
| 2014/0358128 A1 | 12/2014 | Montazeri et al. | |
| 2015/0092191 A1* | 4/2015 | Jung | G01N 21/255 356/306 |
| 2015/0226738 A1 | 8/2015 | Dai et al. | |
| 2016/0003744 A1* | 1/2016 | Chou | G01N 21/6486 435/5 |
| 2016/0299134 A1 | 10/2016 | Denomme et al. | |
| 2016/0312275 A1 | 10/2016 | Blainey et al. | |
| 2016/0355869 A1 | 12/2016 | Blair et al. | |
| 2017/0284935 A1 | 10/2017 | Nudukaife et al. | |
| 2021/0001330 A1 | 1/2021 | Quan et al. | |

FOREIGN PATENT DOCUMENTS

| | | |
|---|---|---|
| CN | 106233140 A | 12/2016 |
| CN | 106841188 A | 6/2017 |
| CN | 201880066841.9 | 3/2023 |
| JP | 2011-152108 A | 8/2011 |
| JP | 2014-531043 A | 11/2014 |
| JP | 2015-514225 A | 5/2015 |
| JP | 2016-29400 A | 3/2016 |
| JP | 2017-503483 A | 2/2017 |
| JP | 2020-513860 | 7/2023 |
| KR | 20160128213 A | 11/2016 |
| WO | WO 2004/086044 A1 | 10/2004 |
| WO | WO 2007/022026 A2 | 2/2007 |
| WO | WO 2008/116093 A2 | 9/2008 |
| WO | WO 2013/062540 A1 | 5/2013 |
| WO | WO 2013/154770 A1 | 10/2013 |
| WO | WO 2014/021809 A1 | 2/2014 |
| WO | WO 2015/100373 A2 | 7/2015 |
| WO | WO 2015/130980 A1 | 9/2015 |
| WO | WO 2016/125106 A1 | 8/2016 |
| WO | WO 2016/168386 A1 | 10/2016 |
| WO | WO 2017/124101 A2 | 7/2017 |

OTHER PUBLICATIONS

Hosokawa, Masuo, Naito Makio, Nogi Kiyoshi, Yokoyama Toyokazu, Nanoparticle Technology Handbook Elsevier, Oct. 19, 2007, Science 644 pages, esp p. 365. (Year: 2007).*

(56) References Cited

OTHER PUBLICATIONS

Goncalves et al. (Materials (Basel) Feb. 2010; 3(2): 1420-14650). (Year: 2010).*
Gautam et al. (Journal of Applied Physics 111, 094317 (2012). (Year: 2012).*
International Search Report and Written opinion mailed Aug. 7, 2015 for Application No. PCT/US2015/030125.
International Preliminary Report on Patentability mailed Nov. 24, 2016 for Application No. PCT/US2015/030125.
Hsieh et al., Localized surface plasmon coupled fluorescence fiber-optic biosensor with gold nanoparticles. Anal Chem. May 1, 2007;79(9):3487-93. Epub Mar. 23, 2007.
Kundu et al., Development of evanescent wave absorbance-based fibre-optic biosensor. Pramana—J Phys. Dec. 2010;75: 1099. doi:10.1007/s12043-010-0193-6.
Lepinay et al, Improved detection limits of protein optical fiber biosensors coated with gold nanoparticles. Biosens Bioelectron. Feb. 15, 2014;52:337-44. doi: 10.1016/j.bios.2013.08.058. Epub Sep. 14, 2013.
Lin et al., Tapered optical fiber sensor based on localized surface plasmon resonance. Opt Express. Sep. 10, 2012;20(19):21693-701. doi: 10.1364/OE.20.021693.
Wei et al., Sensitive plasmonic biosensor using gold nanoparticles on a nano fiber tip. Proc. SPIE 6099. Plasmonics in Biology and Medicine III. Feb. 2006;60990J doi:10.1117/12.642541.
Invitation to Pay Additional Fees mailed Apr. 2, 2018 for Application No. PCT/US18/13313.
International Search Report and Written opinion mailed Jun. 1, 2018 for Application No. PCT/US18/13313.
Invitation to Pay Additional Fees mailed Nov. 1, 2018 for Application No. PCT/US18/49883.
International Search Report and Written opinion mailed Jan. 29, 2019 for Application No. PCT/US18/49883.
International Preliminary Report on Patentability for Application No. PCT/US2018/013313 mailed Jul. 25, 2019.
Partial European Search Report mailed Mar. 17, 2021 for Application No. EP 18854207.0.
International Preliminary Report on Patentability mailed Mar. 19, 2020 for Application No. PCT/US18/49883.
Extended European Search Report mailed Jun. 18, 2021 for Application No. EP 18854207.0.
Notice of Supplemental European Search Report mailed Jul. 6, 2021 for Application No. EP 18854207.0.
Chinese Office Action mailed May 5, 2022 for Application No. CN 201880066841.9.
Japanese Office Action mailed Jul. 5, 2022 for Application No. JP 2020-513860.
Kim et al., Interfacing silicon nanowires with mammalian cells. J Am Chem Soc. Jun. 13, 2007;129(23):7228-9. doi: 10.1021/ja071456k. Epub May 22, 2007.
Makvandi et al., Engineering Microneedle Patches for Improved Penetration: Analysis, Skin Models and Factors Affecting Needle Insertion. Nano-Micro Letters. Nov. 16, 2020;13(93):1-41.
Ryu et al., Nanoneedle insertion into the cell nucleus does not induce double-strand breaks in chromosomal DNA. J Biosci Bioeng. Sep. 2013;116(3):391-6. doi: 10.1016/j.jbiosc.2013.03.022. Epub May 3, 2013.
Soo et al., A simple gold nanoparticle probes assay for identification of *Mycobacterium tuberculosis* and *Mycobacterium tuberculosis* complex from clinical specimens. Mol Cell Probes. Oct. 2009;23(5):240-6. doi: 10.1016/j.mcp.2009.04.006. Epub May 20, 2009.

U.S. Appl. No. 16/644,148, filed Mar. 2, 2020, Quan et al.
Chinese Office Action mailed Mar. 16, 2023 for Application No. CN 201880066841.9.
Chinese Office Action mailed Aug. 31, 2023 for Application No. CN 201880066841.9.
Japanese Office Action mailed Jul. 11, 2023 for Application No. JP 2020-513860.
Langer et al., Present and Future of Surface-Enhanced Raman Scattering. ACS Nano. Jan. 28, 2020;14(1):28-117. doi: 10.1021/acsnano.9b04224. Epub Oct. 8, 2019.
Nath et al., A colorimetric gold nanoparticle sensor to interrogate biomolecular interactions in real time on a surface. Anal Chem. Feb. 1, 2002;74(3):504-9. doi: 10.1021/ac015657x.
Chinese Office Action mailed Oct. 19, 2022 for Application No. CN 201880066841.9.
Japanese Office Action mailed Nov. 24, 2022 for Application No. JP 2020-513860.
Alimardani et al., Microneedle Arrays Combined with Nanomedicine Approaches for Transdermal Delivery of Therapeutics. J Clin Med. Jan. 6, 2021;10(2):181. doi: 10.3390/jcm10020181.
Davis et al, Insertion of microneedles into skin: measurement and prediction of insertion force and needle fracture force. J Biomech. Aug. 2004;37(8):1155-63. doi: 10.1016/j.jbiomech.2003.12.010.
Ingrole et al., Microneedle Coating Methods: A Review with a Perspective. J Pharmacol Exp Ther. Sep. 2019;370(3):555-569. doi: 10.1124/jpet.119.258707. Epub Jun. 7, 2019.
Waghule et al., Microneedles: A smart approach and increasing potential for transdermal drug delivery system. Biomedicine and Pharmacotherapy. Jan. 2019; 109:1249-1258. doi.org/10.1016/j.biopha.2018.10.078.
Chinese Office Action mailed Feb. 1, 2024 for Application No. CN 201880066841.9.
Chinese Office Action mailed Aug. 24, 2024 for Application No. CN 201880066841.9.
Japanese Office Action mailed Jan. 9, 2024 for Application No. JP 2023-045563.
Japanese Office Action mailed Aug. 6, 2024 for Application No. JP 2023-045563.
[No Author Listed], Creating a Pipette with a Short Taper and a 25µ to 35µ Tip. https://www.sutter.com/PDFs/short.pdf [last accessed Jul. 28, 2024].
[No Author Listed], How to Choose a Puller. WPI Infographic. https://www.wpiinc.com/pub/media/wysiwyg/pdf/ infographics/Puller-Comparison_IG.pdf [last accessed Jul. 28. 2024].
[No Author Listed], Sutter Instrument 50 Years. Sutter Catalog; p. 1-371. https://www.sutter.com/PDFs/SutterCatalog.pdf [last accessed Jul. 28. 2024].
Bafna et al., Fabrication of Low Noise Borosilicate Glass Nanopores for Single Molecule Sensing. PLoS One. Jun. 10, 2016;11(6):e0157399. doi: 10.1371/journal.pone.0157399.
Brown et al., Making patch-pipettes and sharp electrodes with a programmable puller. J Vis Exp. Oct. 8, 2008;(20):939. doi: 10.3791/939.
Gierahn et al., Seq-Well: portable, low-cost RNA sequencing of single cells at high throughput. Nat Methods. Apr. 2017; 14(4):395-398. doi: 10.1038/nmeth.4179. Epub Feb. 13, 2017.
Wang, Application of a multifunctional composite material based on Gold Nanorods (GNRs) in the diagnosis and treatment of oral cancer. Chinese Doctoral Dissertations Full-text Database Engineering Science and Technology I. Jul. 2016;(7):30-37.

* cited by examiner

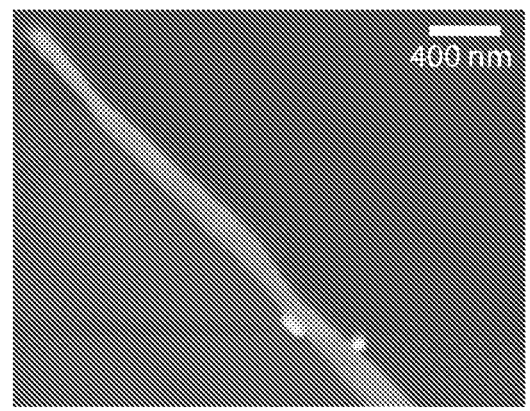
Fig. 7A
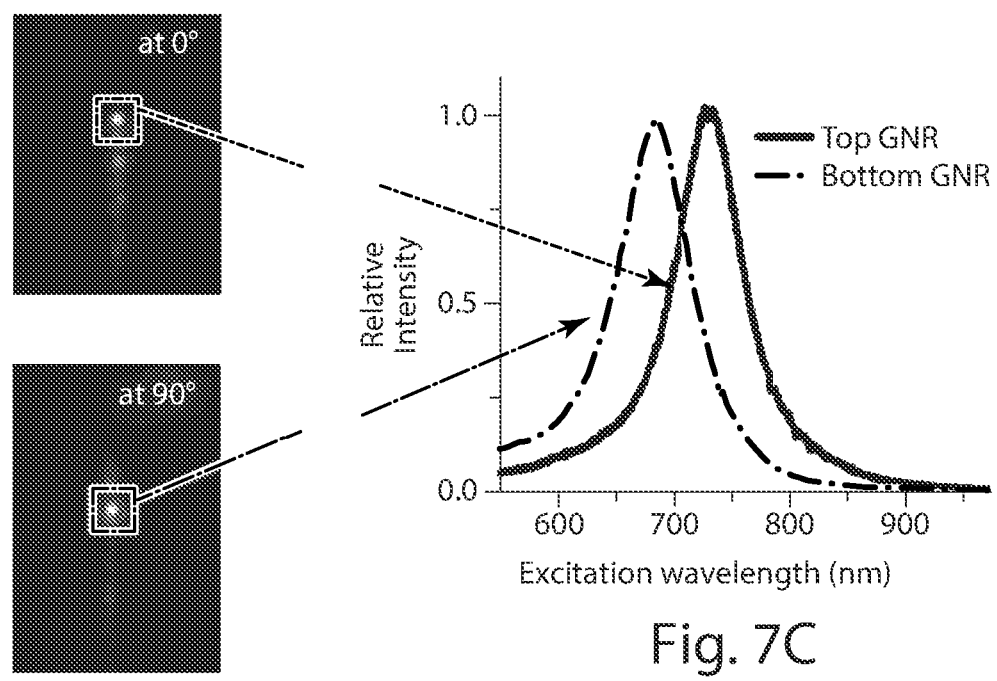
Fig. 7B
Fig. 7C

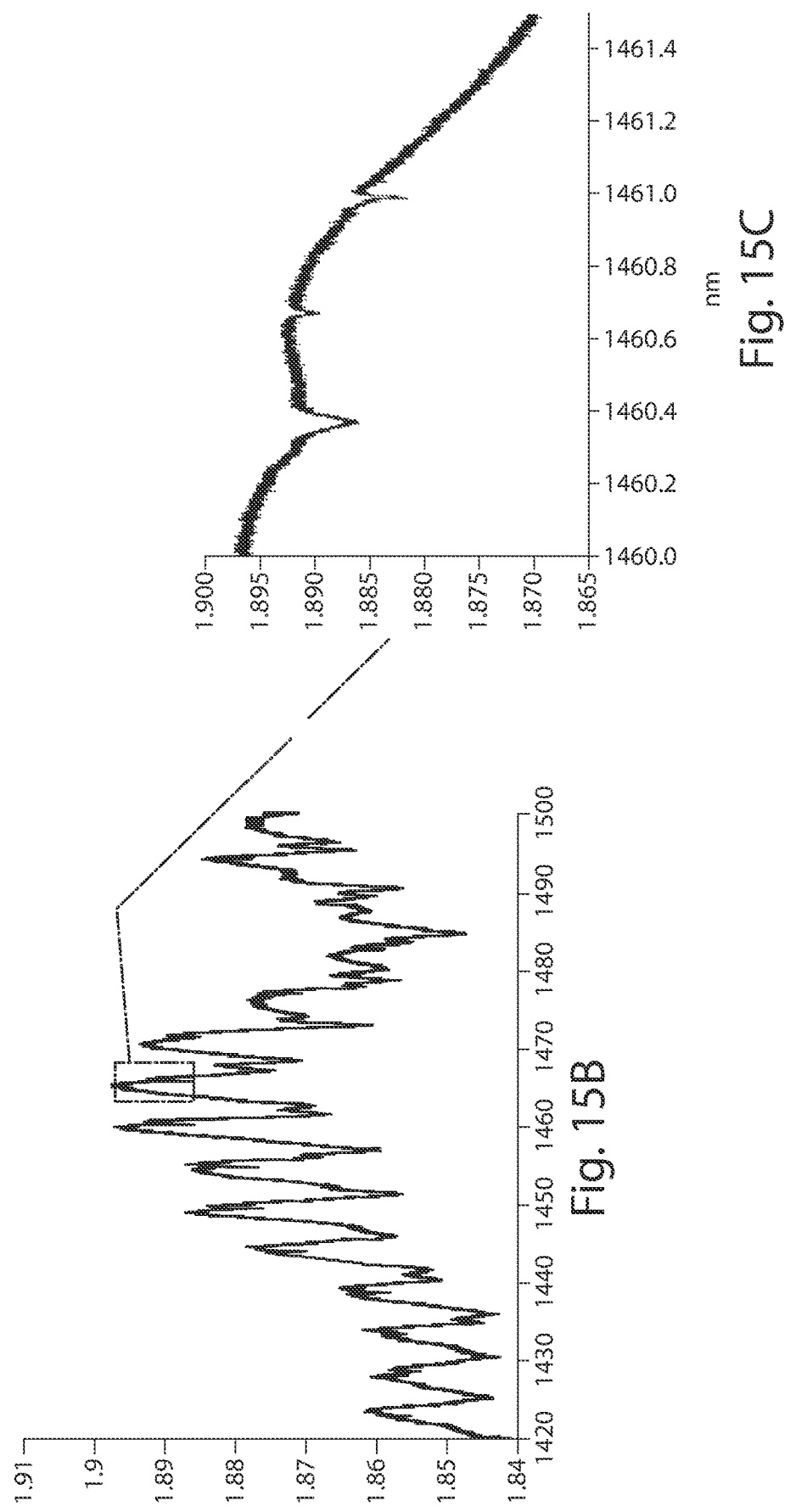

Gold nanorod solution flow

SYSTEMS AND METHODS FOR MAKING AND USING SENSORS, PROBES, AND OTHER DEVICES

RELATED APPLICATIONS

This application is a National Stage Filing under 35U.S.C. § 371 of International Application No. PCT/US2015/030125, filed May 11, 2015, entitled "Systems and Methods for Making and Using Sensors, Probes and Other Devices," which claims the benefit of U.S. Provisional Patent Application Ser. No. 61/991,842, filed May 12, 2014, entitled "Systems and Methods for Making and Using Sensors, Probes and Other Devices," by Quan, et al., each of which is incorporated herein by reference in its entirety.

FIELD

The present invention generally relates, in some aspects, to systems and methods for making and using sensors, including nanoprobe sensors, or other devices.

BACKGROUND

Fluorescent imaging technology has been extensively used to study living cells, including protein function, metastatic processes, and signaling networks. However, reliable fluorophore labeling is laborious and challenging, for example, as proteins are dynamically synthesized and redistribute inside the cells. De novo expression of fluorescent proteins, such as green fluorescent proteins (GFP), can be difficult to implement for non-transfectable cells, and labels can change protein dynamics, especially with proteins where slight modification of the proteins might change the dynamics of the signaling, and further affect the cell response. One example is the tumor suppressor p53, which has been widely regarded as a key target for cancer therapy. Thus, improvements are needed.

SUMMARY

The present invention generally relates, in some aspects, to systems and methods for making and using sensors, including nanoprobe sensors, or other devices, such as optical components. The subject matter of the present invention involves, in some cases, interrelated products, alternative solutions to a particular problem, and/or a plurality of different uses of one or more systems and/or articles.

In one aspect, the present invention is generally directed to an article. In one set of embodiments, the article comprises a member comprising a starting portion, an end portion, and a tapered portion connecting the starting portion to the end portion. In some cases, the starting portion has an average cross-sectional diameter of at least about 100 micrometers, the end portion has an average cross-sectional diameter of between about 100 nm and about 2 micrometers and a length of between about 2 micrometers and about 3 mm, and the tapered portion has a length of no more than about 500 micrometers. In addition, in certain embodiments, at least one particle is immobilized relative to the end portion of the member.

According to another set of embodiments, the article comprises a member having a first starting portion, a second starting portion, and a transition portion connecting the first starting portion to the second starting portion. In some cases, the first and second starting portions each have an average cross-sectional diameter of at least about 100 micrometers, and the transition portion has a smallest cross-sectional diameter of between about 50 nm and about 2 micrometers and a length of no more than about 2 mm.

The article, in still another set of embodiments, includes a member comprising a starting portion, an end portion, and a tapered portion connecting the starting portion to the end portion. In some embodiments, the starting portion has an average cross-sectional diameter of at least about 100 micrometers, the end portion has an average cross-sectional diameter of no more than about 100 nm and a length of at least about 2 micrometers, and the tapered portion has a length of no more than about 500 micrometers. In certain cases, the article also comprises a cell, where at least a portion of the end portion of the member is inside the cell.

In yet another set of embodiments, the article comprises a member comprising a starting portion, an end portion, and a tapered portion connecting the starting portion to the end portion. According to some embodiments, the starting portion has an average cross-sectional diameter of at least about 100 micrometers, the end portion has an average cross-sectional diameter of no more than about 100 nm and a length of at least about 2 micrometers, and the tapered portion has a length of no more than about 500 micrometers. In one embodiment, the article also includes an optical component. In some cases, the member is positioned to deliver light to the optical component.

The article, in another set of embodiments, includes a member having a first starting portion, a second starting portion, and an transition portion connecting the first starting portion to the second starting portion. In some embodiments, the first and second starting portions each have an average cross-sectional diameter of at least about 100 micrometers, and the transition portion has a minimum cross-sectional diameter ranging from 50 nanometers to 2 micrometers and a length of no more than about 2 mm. The article may also comprise a substrate comprising an optical component. In some cases, the member is positioned to deliver light to the optical component.

In another aspect, the present invention is generally directed to a method. In one set of embodiments, the method includes an act of determining the vibration amplitude and/or frequency of a member comprising a starting portion, an end portion, and a tapered portion connecting the starting portion to the end portion. In some cases, the starting portion has an average cross-sectional diameter of at least about 100 micrometers, the end portion has an average cross-sectional diameter of between about 100 nm and about 2 micrometers and a length of between about 2 micrometers and about 3 mm, and the tapered portion has a length of no more than about 500 micrometers.

The method, in accordance with another set of embodiments, includes an act of determining the vibration amplitude and/or frequency of a member comprising a member having a first starting portion, a second starting portion, and a transition portion connecting the first starting portion to the second starting portion. In some cases, the first and second starting portions each have an average cross-sectional diameter of at least about 100 micrometers, and the transition portion has a smallest cross-sectional diameter of between about 50 nm and about 2 micrometers and a length of no more than about 2 mm.

In yet another set of embodiments, the method includes acts of partially exposing a member to etchant media comprising an etchant that etches the member, removing the member from the etchant media when a portion of the member has been etched to have an average cross-sectional diameter of no more than about 100 micrometers, and optionally, immobilizing at least one particle onto the etched portion of the member.

Still another set of embodiments are generally directed to a method comprising acts of exposing a member having a first end and a second end to etchant media such that the first end and the second end are not in contact with the etchant media, and removing the member from the etchant media when a portion of the member has been etched to have an average cross-sectional diameter of between about 50 nm and about 2 micrometers.

In one set of embodiments, the method includes acts of partially exposing a member to etchant media that etches the member. In some instances, the etchant media comprises a first phase comprising an etchant, a second phase comprising an oil positioned above the first phase, and a third phase comprising a polar fluid positioned above the second phase.

The method, in another set of embodiments, includes acts of partially exposing a member to etchant media comprising an etchant that etches the member, and altering the concentration of etchant within the etchant media while the member is exposed to the etchant media.

In still another set of embodiments, the method includes acts of partially inserting a member into a cell. In some cases, the member comprises a starting portion, an end portion, and a tapered portion connecting the starting portion to the end portion. In one embodiment, the starting portion has an average cross-sectional diameter of at least about 100 micrometers, the end portion has an average cross-sectional diameter of between about 100 nm and about 2 micrometers and a length of between about 2 micrometers and about 3 mm, and the tapered portion has a length of no more than about 500 micrometers.

The method, in yet another set of embodiments, includes acts of partially inserting a member into a cell, the member comprising a starting portion and a tapered portion, and determining a characteristic of the cell using light propagated through the member. In some embodiments, the starting portion has an average cross-sectional diameter of at least about 100 micrometers, and the tapered portion has a length of no more than about 500 micrometers.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 7A-7C illustrate surface plasmon resonance using a member, in yet another embodiment of the invention;

FIGS. 15A-15C illustrate characterization of a device in yet another embodiment of the invention;

DETAILED DESCRIPTION

Figure 1A:
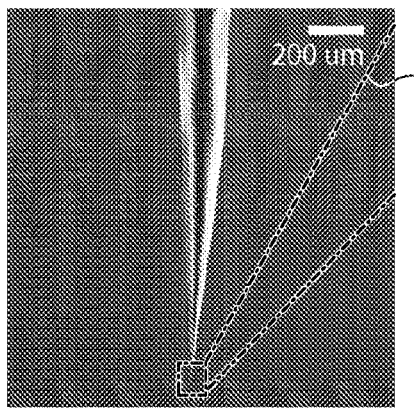
FIGS. 1A-1I illustrate various members in accordance with certain embodiments of the invention.

The present invention generally relates, in some aspects, to systems and methods for making and using sensors or other devices, such as optical components. One aspect is generally directed to a sensor or other device comprising a nanometer-sized portion. In some embodiments, the sensor can be used to determine various characteristics such as temperature, humidity, an electric field, a magnetic field, an analyte, or the like. For instance, in one embodiment, a portion of a sensor device may be inserted into a cell and used to study the cell, e.g., using optical techniques such as surface plasma resonance. In some embodiments, such sensors or other devices may comprise metal, glass, or other materials, which can be prepared using etching or other techniques.

One aspect of the invention is now described with reference to FIG. 1. In FIG. 1F, a schematic diagram of a member 10 is shown, including a starting portion 12, a tapered portion 14, and an end portion 16. The end portion may be nanometer-sized in various embodiments. Member 10 may form part of a probe, a sensor, or another device as is discussed herein. It should also be understood that this figure is schematic and not intended to be drawn to scale; in addition, in some cases, other portions or components may be present within member 10 and/or immobilized relative to member 10 as well, for example, as discussed below. Member 10 may include any suitable material. For instance, member 10 may be formed a metal (e.g., nickel or silicon), silica, glass, or the like. In some cases, member 10 is formed from a unitary material, e.g., produced through etching or other techniques. Member 10 may also be able to transmit light in some embodiments.

Starting portion 12 of member 10 may have any suitable cross-sectional shape, e.g., square or circular, and in some cases, starting portion 12 has substantially the same cross-sectional area within the starting portion. Typically, starting portion 12 has a larger cross-sectional area than tapered portion 14 or end portion 16. In some cases, starting portion may be connected to other portions or components, e.g., as discussed below. As a non-limiting example, in one embodiment, member 10 may be in optical communication with a fiber optic cable, e.g., such that a portion of the member may be determined using an optical sensor via the fiber optical cable.

End portion 16 may also have any suitable cross-sectional shape or area, and the cross-sectional shape may be the same or different from starting portion 12. For example, end portion 16 may be substantially circular in some cases. Typically, end portion 16 has a smaller cross-sectional area than starting portion 12. In some cases, end portion 16 may have a relatively constant cross-sectional area, although it should be understood that end portion 16 may not necessarily be perfectly circular or cylindrical in reality. End portion 16 may also have any suitable length, e.g., a length of at least about 1 micrometers, or other lengths as discussed herein. In addition, it should be understood that in some embodiments, no end portion is present.

Also shown in FIG. 1F is tapered portion 14, connecting starting portion 12 to end portion 16. The tapered portion may be relatively smooth or linear, or have other slopes between starting portion 12 and end portion 16, e.g., as is shown in FIG. 1G. Thus, in certain embodiments, the transition between the tapered portion and either or both starting portion 12 and end portion 16 may not necessarily be abrupt or precisely-defined (e.g., as is shown in FIG. 1F); instead, the transition may be relatively gradual as is shown in FIG. 1G, although the tapered portion 14 may still be readily identified, e.g., as a portion where the average cross-sectional area changes between a first value (e.g., defined by starting portion 12) and a second value (e.g., defined by end portion 16). Additionally, tapered portion 14, in some embodiments, is relatively small, e.g., having a length of 500 micrometers or less. Surprisingly, such relatively short dimensions are difficult to achieve using conventional technologies, such as drawing glass rods to produce optical fibers; for instance, drawing technologies usually result in long (often meters) tapered portions instead. However, in some embodiments of the present invention as discussed herein, relatively short tapered sections may be produced.

In addition, in some cases, more than one starting portion may be present in the member, e.g., with a transition portion between the starting portions. An example may be seen in FIG. 1H, with starting portions 12 and 13 on either side of transition portion 18. The starting portions may have the same, or different lengths and/or average cross-sectional diameters, and these may each independently be any of the dimensions discussed herein. The transition portion typically has a smaller average cross-sectional diameter.

As mentioned, such members may form part of a probe, a sensor, or another device, and thus, such members can be used for a variety of purposes. In one set of embodiments, for example, member 10 can be formed from an optical fiber or other light-transmitting material and used to guide or direct light. For instance, light may be applied to starting portion 12, and directed via tapered portion 14 and end portion 16 to a relatively small or focused region, e.g., on a sample (e.g., a biological sample such as a cell) or on an optical component, etc. In some cases, the light may be used to analyze the sample or a portion of the sample, e.g., using techniques such as surface plasmon resonance (SPR), surface-enhanced Raman spectroscopy (SERS), or other techniques described herein. One or more particles may also be attached or immobilized relative to end portion 16, which can be used to facilitate analysis in certain embodiments.

In addition, in some embodiments, member 10 may be vibrated, and its vibration characteristics such as amplitude and/or frequency can be determined, e.g., optically. The vibration characteristics of the member may be affected by the presence of other portions or components, and this may be used, for example, as a sensor. For instance, one or more reaction entities sensitive to an analyte may be immobilized relative to end portion 16, such that binding or other interaction between an analyte and a reaction entity may alter the vibration of end portion 16. Thus, for example, an antibody can be used for detection of a protein or other antigen, platinum can be used for detection of hydrogen, or a hydrogel can be used for detection of water (e.g., to determine humidity). In some cases, even relatively small amounts of analyte binding may result in determinable changes in certain vibration characteristics. Other non-limiting examples are discussed in more detail below.

In some cases, members such as those shown in FIG. 1F or FIG. 1G may be formed using various etching techniques. Referring now to FIG. 1I, as an example, member 10 may be partially exposed or immersed to etchant media 20 comprising an etchant that is able to etch the member. In some cases only a portion of the member is exposed to the etchant such that only a portion of the member is etched, e.g., to produce an end portion 16 and an unetched portion (or a starting portion) 12. In some cases, the etchant media may also from a meniscus 22 around the member, which may result in partial etching of the member to produce a tapered portion 14 of the member. For example, in some embodiments, a concave meniscus is formed, e.g., due to surface tension effects, and the concave meniscus may partially "climb" the sides of member 10 during the etching process to form the tapered portion 14. Member 10 can be withdrawn once etching of the member (e.g., to produce an end portion) has progressed to a desired size, as is shown in FIG. 1I. Excess etchant media may subsequently be washed or rinsed off in some cases. Depending on the position of the member (e.g., the angle of insertion) and/or the properties of etchant media (e.g., the surface tension, concentration of etchant, etc.), different taperings can be produced.

Accordingly, various aspects of the invention are directed to sensors or other devices comprising members having certain shapes and/or dimensions as discussed herein. In some embodiments, the members may be formed from one or materials that are susceptible to etching with a suitable etchant. For instance, the member may comprise materials such as silica or glass, which can be etched using HF (hydrofluoric acid) or BOE (buffered oxide etch). As another example, the member may comprise a metal such as copper, iron, nickel, and/or steel, which can be etched using acids such as HCl (hydrochloric acid), $HNO_3$ (nitric acid), sulfuric acid ($H_2SO_4$), and/or other etching compounds such as such as ferric chloride ($FeCl_3$) or copper sulfate ($CuSO_4$). As yet another example, the member may comprise silicon or other semiconductor materials, which can be etched using etchants such as EDP (a solution of ethylene diamine and pyrocatechol), KOH (potassium hydroxide), and/or TMAH (tetramethylammonium hydroxide). The member may also comprise, in some cases, a plastic or a polymer, for example, polymethylmethacrylate, polystyrene, polyperfluorobutenylvinylether, etc., which can be etched using KOH (potassium hydroxide), and/or other acids such as those described herein.

The member may comprise or consist essentially of one material, or more than one material in some embodiments. For instance, in one embodiment, the member is formed from a unitary or a solid piece of material that may be etched as discussed herein. In addition, the member may be relatively stiff, or the member may be flexible or bendable in some cases, depending on the materials forming the member. In some cases, the member may be initially created by pulling a material in a flame or in a laser (e.g., a $CO_2$ laser), e.g., to create an initial taper in the member. For instance, the member, prior to exposure to the etchant media, may have a transition portion connecting the first end to the second end, wherein the transition portion has a maximum cross-sectional diameter of less than about 10 micrometers. However, this is not required, and in other cases, the member is not initially tapered prior to exposure to the etchant media.

The member may also have any suitable shape or size, before and/or after etching. In one set of embodiments, the member may be substantially cylindrical or rod-shaped. The member may have any suitable cross-sectional shape, for example, square, circular, triangular, ellipsoidal, polygonal, a star, an irregular shape, etc. The member may maintain the same cross-sectional shape throughout its length, or there may be different cross-sectional shapes in different portions of the member.

The member may also have any suitable dimension. In some cases, the member may have an average cross-sectional diameter of at least about 1 micrometer, at least about 2 micrometers, at least about 3 micrometers, at least about 5 micrometers, at least about 10 micrometers, at least about 20 micrometers, at least about 30 micrometers, at least about 50 micrometers, at least about 75 micrometers, at least about 100 micrometers, at least about 200 micrometers, at least about 300 micrometers, at least about 500 micrometers, at least about 750 micrometers, at least about 1 mm, at least about 2 mm, at least about 3 mm, at least about 5 mm, at least about 7.5 mm, at least about 10 mm, at least about 20 mm, at least about 30 mm, at least about 50 mm, at least about 75 mm, at least about 100 mm, etc. The cross-sectional dimension of a non-circular cross-sectional shape may be taken as the diameter of a perfect circle having the same area as the cross-sectional shape. In addition, the member can have a cross-sectional area that is substantially the same along the length of the member. However, in some cases, the cross-sectional area may not be substantially the same along the length of the member, although the average cross-sectional area can be determined by mathematically averaging the average cross-sectional areas throughout the member.

The member may also have any suitable length. For instance, the length of the member may be at least about at least about 1 mm, at least about 3 mm, at least about 5 mm, at least about 10 mm, at least about 30 mm, at least about 50 mm, at least about 100 mm, at least about 300 mm, at least about 500 mm, at least about 1 m, at least about 3 m, at least about 5 m, etc.

As noted above, in some cases, the member may comprise various portions, e.g., as determined by etching, or other techniques. For instance, in one set of embodiments, a member may comprise a starting portion, an end portion, and a tapered portion. In another set of embodiments, a member may comprise a transition portion as discussed herein. In one set of embodiments, a member can be formed by partially exposing the member to an etchant, where the starting portion is not substantially exposed to the etchant, while the end portion is exposed to the etchant (e.g., submerged) and the tapered portion is partially exposed to the etchant, e.g., via a meniscus. It is to be noted that in some cases, however, the transitions between these regions are not sharp or mathematically precise.

The starting portion, which may be the unetched portion of the member, may have any of the shapes, dimensions, or average cross-sectional diameters discussed above for the member. In addition, in some embodiments, the starting portion may be relatively large, compared to other portions of the member. In some cases, the starting portion may have a length of at least about at least about 1 mm, at least about 3 mm, at least about 5 mm, at least about 10 mm, at least about 30 mm, at least about 50 mm, at least about 100 mm, at least about 300 mm, at least about 500 mm, at least about 1 m, etc.

Other portions of the member, in contrast, may be smaller than the starting portion, at least in cross-sectional area or dimension. For instance, in some cases, an end portion or a transition portion of the member may have an average cross-sectional dimension that is less than about 50%, less than about 40%, less than about 30%, less than about 25%, less than about 20%, less than about 15%, less than about 10%, or less than about 5% of the average cross-sectional dimension of the starting portion.

In some cases, an end portion or a transition portion may have an average cross-sectional diameter of no more than about 50 micrometers, no more than about 40 micrometers, no more than about 30 micrometers, no more than about 25 micrometers, no more than about 20 micrometers, no more than about 15 micrometers, no more than about 10 micrometers, no more than about 5 micrometers, no more than about 3 micrometers, no more than about 2 micrometers, no more than about 1 micrometer, no more than about 750 nm, no more than about 500 nm, no more than about 250 nm, no more than about 100 nm, no more than about 75 nm, no more than about 50 nm, etc. In some cases, an end portion or a transition portion may have an average cross-sectional diameter that is at least about 50 nm, at least about 75 nm, at least about 100 nm, at least about 250 nm, at least about 500 nm, at least about 750 nm, at least about 1 micrometer, at least about 3 micrometers, at least about 5 micrometers, at least about 10 micrometers, at least about 15 micrometers, at least about 20 micrometers, at least about 25 micrometers, at least about 30 micrometers, at least about 40 micrometers, at least about 50 micrometers, etc. In addition, combinations of any of these are also possible; for example, the average cross-sectional diameter may be between about 100 nm and about 2 micrometers.

An end portion or a transition portion may also have any suitable shape or cross-sectional area. In some cases, the end portion or the transition portion is substantially cylindrical or rod-shaped, or the end portion may have a circular cross-sectional shape. The end portion or the transition portion may be straight, or bent or curved in some cases. The end portion or the transition portion may have the same cross-sectional dimension throughout its length, or there may be slight variations in cross-sectional shape or dimension, e.g., due to imperfections in the formation process, or due to intentional variations. In some cases, a minimal cross-sectional area or dimension of an end portion or a transition portion may be greater than about 80%, greater than about 85%, greater than about 90%, greater than about 95%, or greater than 97% of the average cross-sectional area or dimension of the end portion or the transition portion.

Certain embodiments of the present invention are generally directed to end portions or transition portions that are relatively long. For instance, an end portion or a transition portion may have a length of at least about 50 nm, at least about at least 100 nm, at least about 200 nm, at least about 300 nm, at least about 500 nm, at least about 1 micrometer, at least about 2 micrometers, at least about 3 micrometers, at least about 5 micrometers, at least about 10 micrometers, at least about 20 micrometers, at least about 30 micrometers, at least about 50 micrometers, at least about 75 micrometers, at least about 100 micrometers, at least about 200 micrometers, at least about 300 micrometers, at least about 500 micrometers, at least about 750 micrometers, at least about 1 mm, at least about 2 mm, at least about 3 mm, at least about 5 mm, at least about 7.5 mm, at least about 10 mm, etc. In some cases, however, an end portion or a transition portion may have a length of no more than about 10 mm, no more than about 7.5 mm, no more than about 5 mm, no more than about 3 mm, no more than about 2 mm, no more than about 1 mm, no more than about 750 micrometers, no more than about 500 micrometers, no more than about 300 micrometers, no more than about 200 micrometers, no more than about 100 micrometers, no more than about 75 micrometers, no more than about 50 micrometers, no more than about 30 micrometers, no more than about 20 micrometers, no more than about 10 micrometers, no more than about 5 micrometers, no more than about 3 micrometers, no more than about 2 micrometers, no more than about 1 micrometer, no more than about 500 nm, no more than about 300 nm, no more than about 200 nm, no more than about 100 nm, no more than about 50 nm, etc. Combinations of any of these are possible, e.g., a length of between about 2 micrometers and about 3 mm. Surprisingly, relatively long end or transition portions, often having substantially constant and narrow diameters, are difficult to fabricate using conventional technologies.

Between the end portion and the starting portion may be a tapered portion or a transition region. The taper between the end portion and the starting portion may be relatively smooth in some cases, and may present a linear profile, or a non-linear or curved profile in some cases, e.g., as is shown in FIGS. 1F and 1G. In some cases, the tapered portion is substantially frustroconical shaped or a "truncated cone" shape.

The tapered portion may be relatively short in some cases. However, relatively short taper regions have not been successfully achieved in the past; for example drawing technologies, where a rod of material is heated and pulled apart to form a tapered portion leading to a smaller diameter, generally results in tapering lengths measured on the order of meters.

However, certain embodiments of the invention are directed to lengths of the tapered portion of less than about 1 m, less than about 300 mm, less than about 100 mm, less than about 30 mm, less than about 10 mm, less than about 3 mm, less than about 1 mm, less than about 500 micrometers, less than about 300 micrometers, less than about 100 micrometers, less than about 50 micrometers, less than about 30 micrometers, less than about 10 micrometers, less than about 5 micrometers, less than about 3 micrometers, or less than about 1 micrometer. In addition, in some cases, the tapered region may be at least about 1 micrometer, at least about 3 micrometers, at least about 5 micrometers, at least about 10 micrometers, at least about 30 micrometers, at least about 50 micrometers, at least about 100 micrometers, at least about 300 micrometers, at least about 500 micrometers, at least about 1 mm, at least about 3 mm, at least about 5 mm, at least about 10 mm, at least about 30 mm, at least about 100 mm, etc. Combinations of any of these are also possible; for instance, the tapered region may have a length of between about 100 micrometers and about 500 micrometers.

The end portion or the transition portion may have any suitable cross-sectional shape, for example, square, circular, triangular, ellipsoidal, polygonal, a star, an irregular shape, etc. The end portion or the transition portion may have a profile that is linear, or non-linear or curved profile in some cases. In some cases, the profile may be irregular. Examples of end portions with various profiles can be seen in FIGS. 1F and 1G, and examples of transition portions with various profiles can be seen in FIGS. 1H and 1I. For instance, FIG. 1H shows starting portions 12 and 13 on either side of transition portion 18. The starting portions may have the same, or different lengths and/or average cross-sectional diameters, and these may each independently be any of the dimensions discussed herein. The transition portion typically has a smaller average cross-sectional diameter.

In addition, in some embodiments, as is shown in FIG. 1I, a transition portion may be formed of tapered portions 14 and 15, and a central region 19. Tapered portions 14 and 15 may each independently have any of the shapes or sizes previously discussed herein, and central region 19 may have any of the shapes or sizes previously discussed herein with respect to end portions. In addition, tapered portions 14 and 15 may be of the same, or different, shapes and/or sizes. For example, the average cross-sectional diameters may differ by no more than about 1 micrometer, no more than about 750 nm, no more than about 500 nm, no more than about 250 nm, no more than about 100 nm, no more than about 50 nm, no more than about 30 nm, no more than about 10 nm, etc.

As mentioned, in some cases, one, two, or more particles may be fastened or immobilized to the member, e.g., to an end portion, transition portion, or other portions as discussed herein. The particles may be fastened or immobilized on any suitable location, e.g., on a side or end of the end portion. The particle may be fastened or immobilized to the member using adhesives, or other techniques such as those discussed herein. The particles may be of any shape or size, and if more than one particle is present, the particles may be of substantially the same shape and/or size, and/or different shapes and/or sizes. The particles may be substantially spherical, or non-spherical in some cases. For example, the particles may include nanorods or elongated structures, having any suitable aspect ratio (largest dimension to smallest dimension, e.g., about 1:1, about 2:1, about 3:1, about 5:1, about 10:1, etc. The particles may be formed from any suitable material. In one set of embodiments, the particles comprise a metal (gold, silver, copper, etc.), a polymer (e.g., polyethylene), silica or glass, etc. In one embodiment, the particle is a nano-diamond. Many such particles may be readily obtained commercially.

Those of ordinary skill in the art will be able to determine the average cross-sectional diameter of a single particle and/or a plurality of particles, for example, using laser light scattering, microscopic examination, or other known techniques. The average cross-sectional diameter of a single particle, in a non-spherical particle, is the diameter of a perfect sphere having the same volume as the non-spherical particle. The average cross-sectional diameter of a particle (and/or of a plurality or series of particles) may be, for example, less than about 1 mm, less than about 300 micrometers, less than about 100 micrometers, less than about 30 micrometers, less than about 10 micrometers, less than about 3 micrometers, less than about 1 micrometer, less than about 800 nm, less than about 600 nm, less than about 400 nm, less than about 200 nm, less than about 100 nm, etc. The average cross-sectional diameter may also be at least about 100 nm, at least about 200 nm, at least about 400 nm, at least about 600 nm, at least about 800 nm, at least about 1 micrometer, at least about 3 micrometers, at least about 10 micrometers, at least about 30 micrometers, at least about 100 micrometers, at least about 300 micrometers, at least about 1 mm, etc. Combinations of any of these are also possible.

In certain aspects, one or more reaction entities may be immobilized relative to the member, for example, on an end portion, a transition portion, or other portion. The reaction entities may be, for example immobilized relative to or fastened directly to an end or transition portion, and/or to one or particles fastened or immobilized relative to the member, e.g., to an end or transition portion of a member. Examples of particles include those discussed above. In some cases, the reaction entities may coat at least a portion of the member, and/or on at least a portion of a particle, if present. Thus, in some cases, for instance, the particles may be partially or completely coated with a layer of reaction entities.

In one set of embodiments, an analyte may be determined via interaction of the analyte with the reaction entity. The term "reaction entity" refers to any entity that can interact with an analyte in such a manner to cause a detectable change in a property, e.g., of a member, such as a chemical property, an optical property, a mechanical property, a vibration property, etc. The reaction entity can comprise a binding partner to which the analyte binds. The reaction entity, when a binding partner, can comprise a specific or a non-specific binding partner of the analyte. For example, the reaction entity may be a chemical or a biochemical, such as a metal, a nucleic acid, an antibody, an aptamer, a sugar, a carbohydrate, a protein, a polymer, catalyst, a quantum dot, etc. As another example, the reaction entity may comprise platinum, which can be used to determine hydrogen. As yet another example, the reaction entity may comprise a hydrogel, which can be used to determine water or humidity.

The binding partner may be a molecule that can undergo binding with a particular analyte, and includes specific, semi-specific, and non-specific binding partners as is known to those of ordinary skill in the art. The term "specifically binds," when referring to a binding partner (e.g., protein, aptamer, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair, the ligand would specifically and/or preferentially select its receptor from a complex mixture of molecules, or vice versa. An enzyme would specifically bind to its substrate, a nucleic acid would specifically bind to its complement, an antibody would specifically bind to its antigen. Other examples include, nucleic acids that specifically bind (hybridize) to their complement, antibodies specifically bind to their antigen, and the like. The binding may be by one or more of a variety of mechanisms including, but not limited to ionic interactions, and/or covalent interactions, and/or hydrophobic interactions, and/or van der Waals interactions, etc.

Another aspect of the present invention is generally directed to systems and methods of making members such as those discussed herein. In some cases, for example, members may be produced by etching various materials to produce the shapes and/or sizes discussed herein. The choice of etchant may depend based on the materials forming the member. For example, metals such as copper, iron, nickel, steel, etc. can be etched using acids such as HCl (hydrochloric acid), $HNO_3$ (nitric acid), sulfuric acid ($H_2SO_4$), and/or other compounds such as such as ferric chloride ($FeCl_3$) or copper sulfate ($CuSO_4$). As yet another example, silicon or other semiconductor materials can be etched using etchants such as EDP (a solution of ethylene diamine and pyrocatechol), KOH (potassium hydroxide), or TMAH (tetramethylammonium hydroxide). Plastics or polymers such as polymethylmethacrylate, polystyrene, polyperfluorobutenylvinylether, etc., can be etched using KOH (potassium hydroxide), or acids such as those described herein. The etchant may be present in pure form, or present in solution, e.g., in polar solution, at any suitable concentration. Higher concentrations may result in faster etchings, while lower concentrations may result in slower and/or more controlled etchings.

Figure 11:
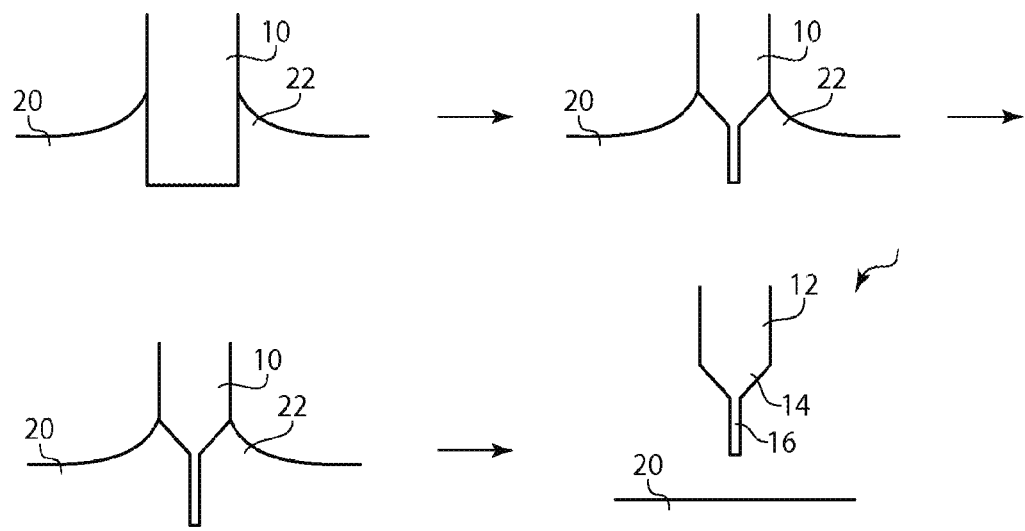
FIG. 11 illustrates the etching of a member, in one embodiment of the invention.
Figure 12A:
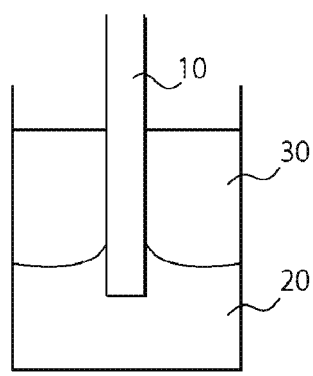
FIG. 12A-12E illustrate various etching techniques, according to still other embodiments of the invention.
Figure 12B:
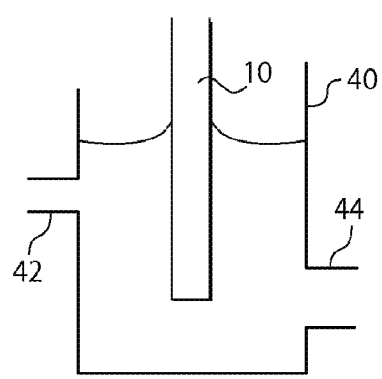
Figure 12C:
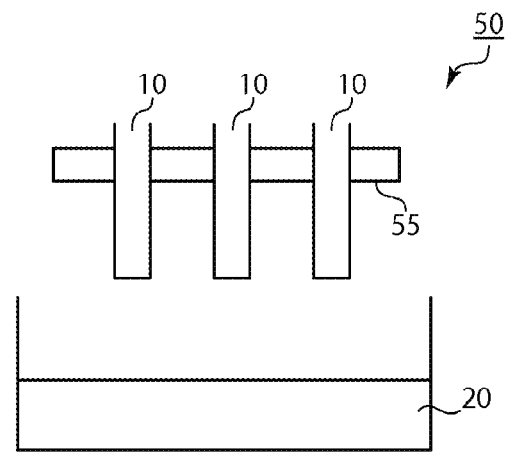
Figure 12D:
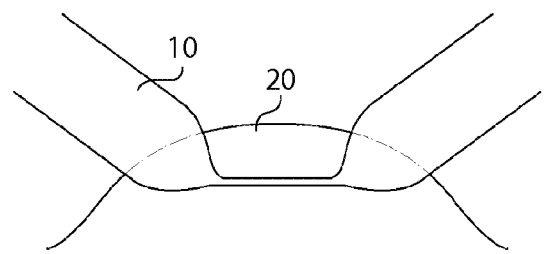
Figure 12E:
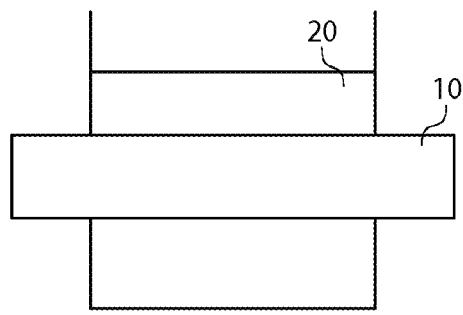

In some cases, a material may be etched by exposing the material to etchant media comprising etchant. The etchant media may also contain other components or phases, e.g., as discussed below. The etchant may be applied to the material using any suitable technique. For example, the etchant may be sprayed, coated, or painted onto the material, or in some cases, a portion of the material may be inserted or submerged into the etchant media, for example, as is shown in FIG. 11. The etchant media may, for example, be contained within a suitable container, or the etchant media may be allowed to "puddle" onto a surface and the material partially exposed to the puddle, e.g., as is shown in FIG. 12D with etchant 20 and member 10. This may be useful, for example, in producing members having two (or more, with multiple "puddles") starting portions surrounding transition portions. As another example, members may be inserted laterally through a container (e.g., through holes within the container) to allow etching of various portions of the member, as is shown in FIG. 12E with member 10 in etchant 20 and container 40.

As previously discussed, in some cases, a meniscus, such as a concave meniscus, may form around the partially exposed material. As the etchant etches the exposed material, a portion of the material may thin or become etched away, e.g., to form an end portion or a transition portion. The meniscus may also cling to the material, e.g., due to surface tension or capillary forces, to produce a tapered region of the material.

The material may be removed before etching is completed, e.g., to produce members having shapes and/or sizes such as those discussed herein. Thus, for example, the member may be removed from the etchant media when a portion of the member has been etched to have an average cross-sectional diameter of no more than about 50 micrometers, no more than about 40 micrometers, no more than about 30 micrometers, no more than about 25 micrometers, no more than about 20 micrometers, no more than about 15 micrometers, no more than about 10 micrometers, no more than about 5 micrometers, no more than about 3 micrometers, no more than about 1 micrometer, no more than about 750 nm, no more than about 500 nm, no more than about 250 nm, or no more than about 100 nm, or the like, or other dimensions as discussed herein.

In some embodiments, the material may be removed before etching for a certain period of time. For example, the material may be exposed to the etchant for at least about 1 sec, at least about 5 sec, at least about 10 sec, at least about 30 sec, at least about 1 min, at least about 2 min, at least about 3 min, at least about 5 min, at least about 10 min, at least about 20 min, at least about 30 min, at least about 40 min, at least about 50 min, at least about 60 min, at least about 75 min, at least about 90 min, at least about 120 min, at least about 180 min, at least about 240 min, etc. In some cases, the amount of time may be no more than about 240 min, no more than about 180 min, no more than about 120 min, no more than about 90 min, no more than about 75 min, no more than about 60 min, no more than about 50 min, no more than about 40 min, no more than about 30 min, no more than about 20 min, no more than about 10 min, no more than about 5 min, no more than about 3 min, no more than about 2 min, no more than about 1 min, no more than about 30 sec, no more than about 10 sec, no more than about 5 sec, or no more than about 1 sec. Combinations of any of these times are also possible, for instance, between about 10 minutes and about 30 minutes.

Figure 17:
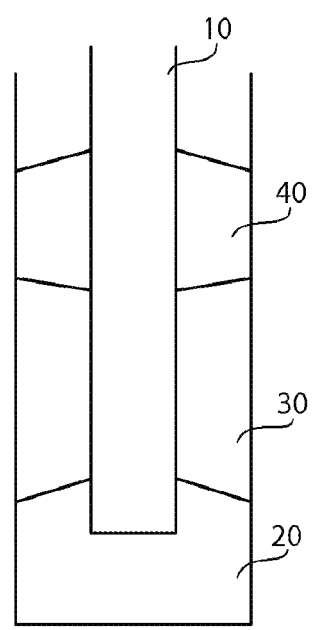
FIG. 17 illustrates etching of a member, in yet another embodiment of the invention.

In some cases, the material may be physically removed from the etchant, or the etchant may be washed or rinsed away. For instance, in one embodiment, the material is removed from the etchant media, then washed or rinsed with a rinsing agent, e.g., with water, a base, an aqueous fluid, a polar fluid, a non-polar fluid, or the like. The polar or aqueous fluid may be, for instance, methanol or acetonitrile. In some embodiments, the rinsing agent may be sprayed onto the material, or the material may be partially or completely immersed in a container containing the rinsing agent. In some cases, e.g., as is shown in FIG. 17, the etchant media itself may include another phase containing the rinsing agent, e.g., positioned above the etchant media, such that upon removal of the material from the etchant, the material is exposed to the rinsing agent, for example, due to the act of moving through the rinsing agent. For example, the etchant media may comprises a first phase comprising an etchant (e.g., in solution), a second phase positioned above the first phase (e.g., as discussed herein), and a third phase comprising a rinsing agent positioned above the second phase.

For example, in some embodiments, another phase of the etchant media may be provided to control the amount of etching. For instance, as is shown in FIG. 12A, a second phase 30 is positioned above a first phase 20 for etching member 10. First phase 20 and second phase 30 may be substantially immiscible with each other, e.g., such that separate phases are produced when the phases are brought together and left undisturbed under ambient conditions (although some degree of miscibility may still occur in some cases). For example, first phase 20 may contain an etchant (e.g., in aqueous solution), while second phase 20 may contain an oil or other material that is substantially immiscible in water. As non-limiting examples, the second phase may comprise benzene, cyclooctane, 2,2,4-trimethylpentane, xylenes such as o-xylene, or the like. In certain embodiments, the second phase can be used to remove any residual etchant from the member upon its removal from the first phase.

In some cases, the material is exposed to a container containing etchant, but the etchant concentration may be altered during the etching process. For instance, as is shown in FIG. 12B, a container 40 containing member 10 and an etchant media may also have an inlet 42 and an outlet 44, through which the etchant media can be controlled, altered, replenished, etc. Thus, for instance, the etchant may be diluted through the addition of a diluting fluid that does not contain etchant, or possibly increased by the addition of additional etchant, or a solution containing higher concentrations of etchant. The diluting fluid may be, for example, water or another aqueous fluid. In addition, in some embodiments, etchant can be removed through the outlet, e.g., during the etching process. Other methods of altering the etchant concentration are also possible. For instance, the etchant media may be changed by batch addition and/or removal of fluids from the container containing the etchant media while etching of the member occurs.

In some cases, a plurality of materials may be simultaneously exposed to an etchant, e.g., as described herein. For example, the materials may be individually applied, or an array of such materials may be formed and simultaneously exposed to an etchant, e.g., within an etchant media. As an example, as is shown in FIG. 12C, a plurality of materials 50 may be exposed to etchant media 20. In some cases, as is shown here, a plurality of members 10 may be immobilized relative to each other, e.g., on a rack or other mechanical immobilization device 55. Thus, a large number of materials may be simultaneously etched in some embodiments, e.g., upon movement of the device. The array may have any suitable number of materials that are etched to produce members, e.g., at least 2, at least 3, at least 5, at least 10, at least 25, at least 50, at least 100, at least 250, at least 500, at least 1000, etc.

Figure 16A:
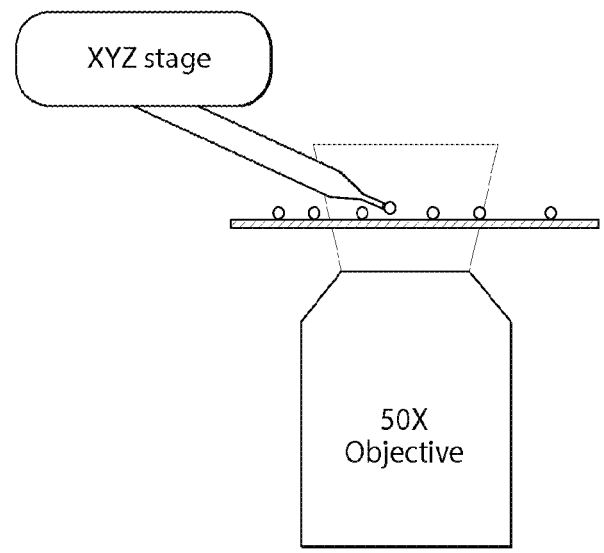
FIGS. 16A-16B illustrate immobilization of particles, in still other embodiments of the invention.
Figure 16B:
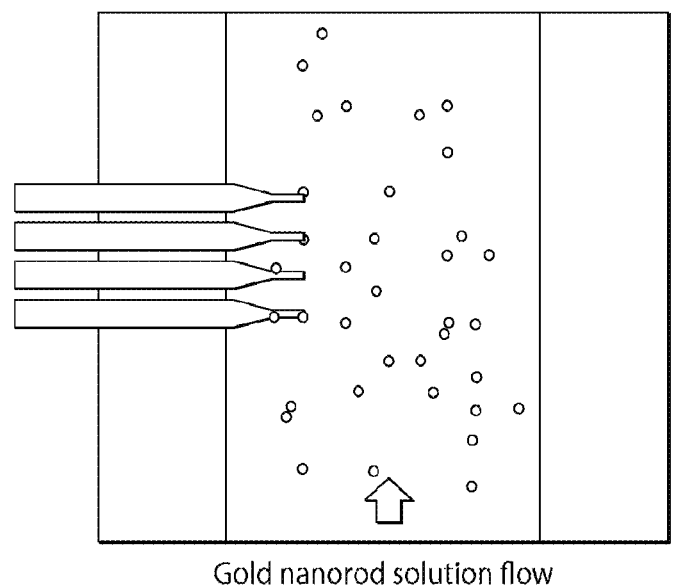

In some cases, one or more particles may be added to the member, e.g. after etching. A variety of particles that can be used, including spherical and non-spherical particles, have been discussed above. In some cases, the particles may be fastened or immobilized to the member via any suitable technique. For instance, in one set of embodiments, e.g., as is shown in FIG. 16A, a particle may be fastened or immobilized relative to the member via an adhesive material positioned between the particle and the member. The adhesive material may be, for example, a polymer or an epoxy. Many such adhesives are commercially available, and include but are not limited to optical adhesives. In some cases, the particle may be fastened or immobilized relative to the end portion via van der Waals or other interactions. In some cases, such as is shown in FIG. 16B, one or more end portions may be positioned within a microfluidic channel containing particle solution, e.g., such that one or more particles may become immobilized onto the end portion. In some cases, one or more reaction entities may be added to the member and/or to particles. The reaction entities may be added using any suitable technique known to those of ordinary skill in the art. For instance, in one set of embodiments, the particles may comprise gold, and reaction entities may be added to the particles via a thiol coupling reaction to the gold, before or after immobilization of the particles to the member.

Members such as those discussed herein may be used in a wide variety of applications and uses, according to various aspects of the invention. For example, in one set of embodiments, a member may be used as a probe for a cell. The member may be partially or completely inserted into a cell. For instance, an end portion of the member may be inserted into a cell (e.g., into the cytoplasm of the cell), and used to interrogate or study at least a portion of the cell. In some cases, this may be performed using light-based techniques, for example, if the member is able to transmit light. Thus, a characteristic of the cell may be determined using light propagated through the member. For instance, light may be used to analyze the cell using techniques such as surface plasmon resonance (SPR) (including localized surface plasmon resonance), or other techniques described herein. In some cases, the member may also contain a reaction entity, e.g., immobilized relative to a portion of a member or a particle immobilized relative to a portion of a member, and the reaction entity. Interaction of the reaction entity with an analyte within the cell may be detectable as discussed herein, e.g., due to change in light or vibration.

The cell may be any suitable cell. The cell may be, for example, a human cell, or other mammalian cell. The cell may also be a bacterium or other single-cell organism, a eukaryotic cell, a plant cell, or an animal cell. Any suitable method of inserting the member into the cell may be used. For example, the member may be inserted into the cell using microinjection, micromanipulation, or other techniques known to those of ordinary skill in the art.

As mentioned, in certain embodiments, the member may be used to optically interrogate or study a sample, for example, a cell. In some cases, a characteristic of the cell or other sample, such as the presence or concentration of an analyte, may interact with the member and/or a reaction entity on the member, which can be determined optically. Examples of optical interrogation techniques that may be used include, but are not limited to, fluorescence, phosphorescence, surface plasma resonance, localized surface plasma resonance, Raman spectroscopy, surfaced-enhanced Raman spectroscopy, or the like.

Figure 4A:
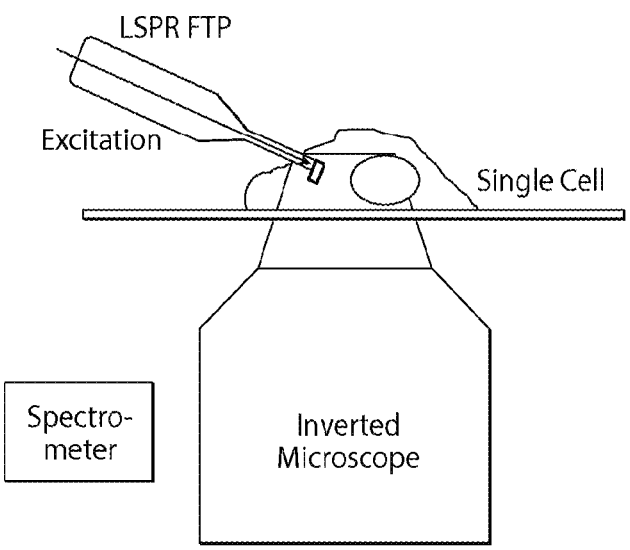
FIGS. 4A-4E illustrate detection of p53 in a cell, in yet another embodiment of the invention.

The member may be used to transmit light to and/or from a sample, such as a cell. For instance, as is shown in FIG. 4A, excitation light may be transmitted to a cell (or other sample) through the member, and emitted light from the sample due to the transmitted light may be detected with a microscope and/or a spectrometer, or other optical detector. In another embodiment, excitation light may be externally transmitted to the cell (or other sample), and the emitted light may be detected through the member. In yet another set of embodiments, excitation light may be externally applied to the sample, while emitted light is also determined through the same member (or through a different member). A variety of suitable optical detectors, including spectrometers, are commercially available.

In another set of embodiments, the member can be positioned to be in optical communication with an optical component. For instance, the member may be positioned to deliver light to the optical component, or to receive light form the optical component. The optical component may be, for example, a waveguide, an optical sensor, an optical detector, an optical fiber, or the like. In some cases, the optical component may be positioned on a substrate, such as a silicon wafer, and the member used to direct light to or from the substrate.

In addition, it should be understood that other techniques may be used to determine an analyte or a characteristic of a sample, in addition or instead of optical techniques. For example, in another set of embodiments, the member may be cantilevered and mechanically vibrated, and characteristics about the vibration of the member may be determined. For instance, the amplitude and/or frequency of the vibration of the member may be determined, e.g., electrically or optically (for example, using a microscope). The vibrations may be induced using a suitable vibrating device, or in some cases, via ambient vibration or thermal noise. Without wishing to be bound by any theory, it is believed that the binding of analytes to a reaction entity immobilized relative to the member (or to particles immobilized to the member) may alter the vibration characteristics of the member, e.g., its amplitude and/or frequency of vibration, and these characteristics may be used to determine the analyte, e.g., the amount or concentration of analyte. For instance, the binding of analytes to a member may alter the weight or weight distribution of the member, and hence affect its vibration characteristics. Thus, for instance, differences in vibration before and after binding of the analyte may be used to determine the presence and/or concentration of the analyte. Any of the analytes and reaction entities discussed herein may be used in various embodiments. For example, hydrogen may be determined based on binding of hydrogen to platinum, while humidity or moister may be determined based on binding of water to a hydrogel, etc.

In some cases, other characteristics can be determined by determining the vibration characteristics of the member, and/or changes in the vibration characteristics of the member. For instance, in some cases, changes in temperature, electric field intensity, magnetic field intensity, etc. may be determined. For example, in some embodiments, nano-diamond particles may be used to sense electric fields, magnetic fields, or temperatures. For instance, nano-diamond particles may comprise nitrogen vacancy (NV) centers that can be in certain spin states as a function of electromagnetic fields and/or temperatures. Accordingly, changes in electric fields, magnetic fields, or temperature may result in changes in spin state, which can be detected, for example, by determining changes in fluorescence activity of the nano-diamond particles, e.g., using members as discussed herein. In addition, in some embodiments, vibration or motion may be imparted to the member using systems and methods such as piezostacks or AC electric fields.

U.S. Provisional Patent Application Ser. No. 61/991,842, filed May 12, 2014, entitled "Systems and Methods for Making and Using Probes and Other Devices," by Quan, et al. is hereby incorporated herein by reference.

The following examples are intended to illustrate certain embodiments of the present invention, but do not exemplify the full scope of the invention.

Example 1

The following examples illustrate a localized surface plasmon resonance (LSPR) fiber tip probe (FTP) system in accordance with certain embodiments of the invention. The following examples also demonstrate label-free detection of intracellular p53. However, the methods described herein may be also widely applicable to other intracellular proteins; p53 is used solely as an example.

The FTP used in this example was a tapered optical fiber that has a sub-5 micrometer length and sub-100 nanometer diameter tip (FIGS. 1A and B). One single gold nanorod (Nanopartz Inc.) was attached to the end of the tip, and the surface of which was functionalized with antibodies specific to the target analyte proteins. The collective oscillation of the conductive electrons in the gold nanorod couples strongly to polarized light in the visible wavelength range, generating a LSPR signal. The light, strongly localized at the surface of the gold nanorod, was sensitive to small perturbations to its optical mode near its surface. Therefore, by monitoring the resonance shift of the LSPR, one can quantify the binding of analyte proteins to the sensor surface. Due to the nanoscale size of the tip and the immobilization of a gold nanorod at its end, the FTP only needed minimal invasiveness with insertion into the cell membrane without affecting its cellular physiology.

Figure 1B:
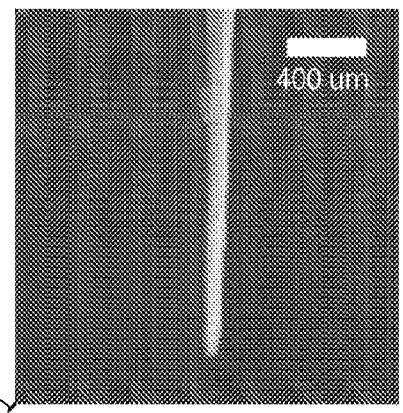
Figure 1C:
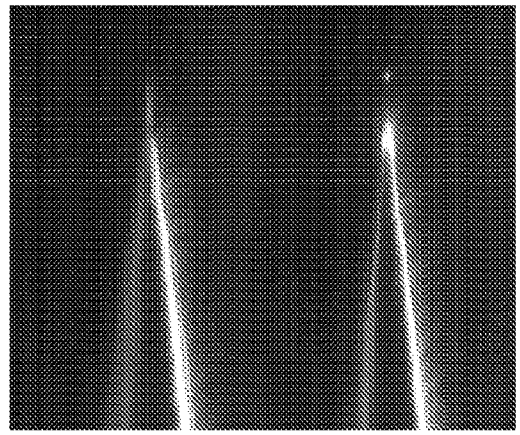
Figure 1D:
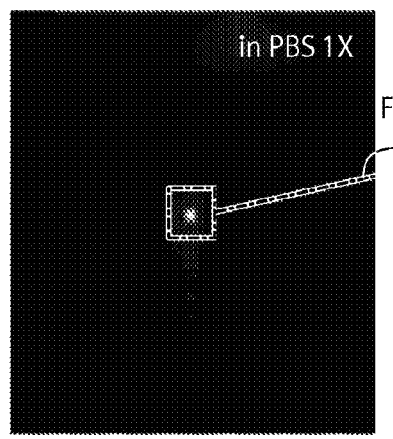
Figure 1E:
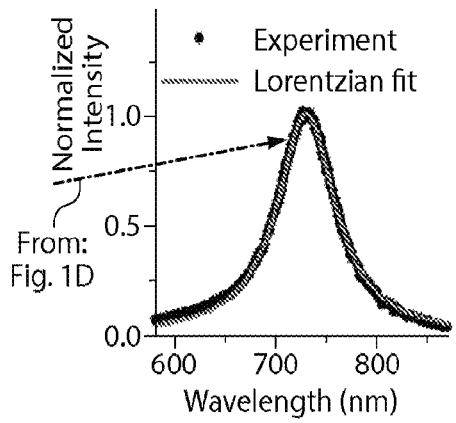
Figure 1F:
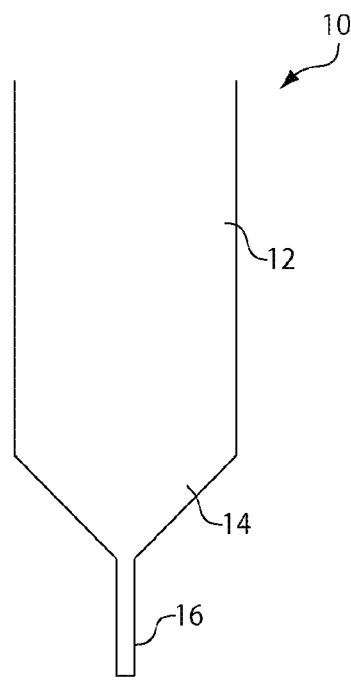
Figure 1G:
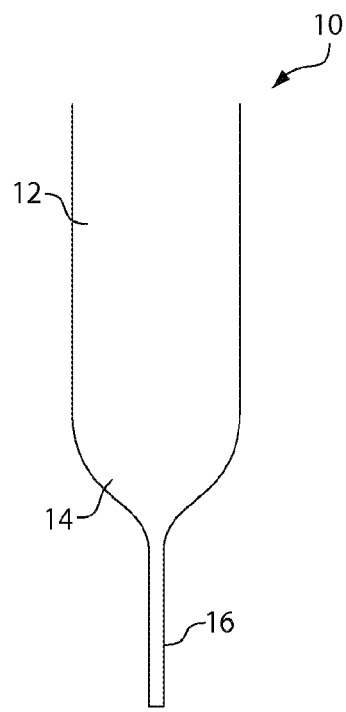
Figure 1H:
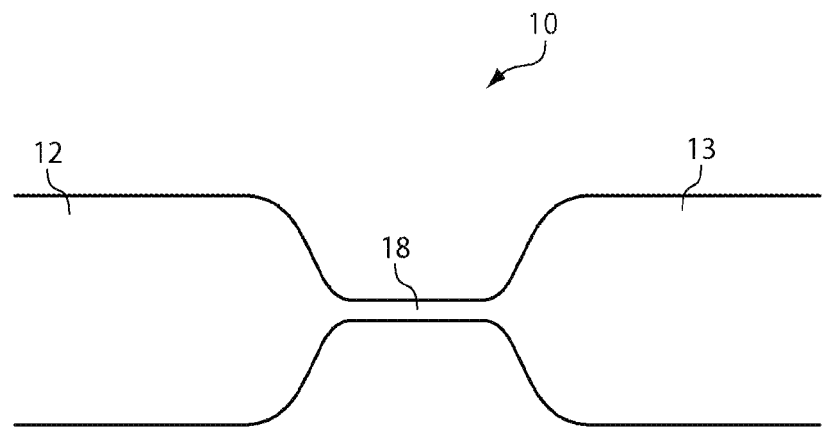
Figure 1I:
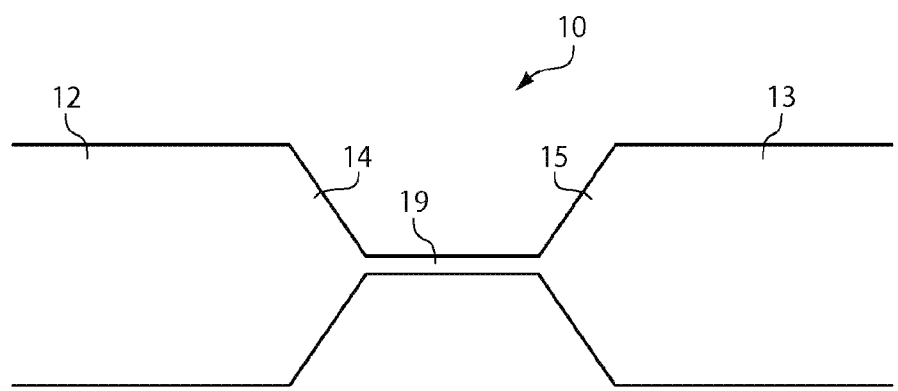

A scanning electron microscope (SEM) image of the FTP is shown in FIG. 1A. A zoomed image of its nanosize tip, attached with a single gold nanorod is shown in FIG. 1B. A white light source (a halogen lamp) was connected to the fiber and excited the LSPR of the gold nanorod at the tip. The resonant scattering signal (in FIG. 1C) from a gold nanorod on the tip can be clearly seen by eye. The resonant scattering signal was collected via 50× objective and was coupled to a spectrometer (Princeton Instrument). FIG. 1D shows the image on the spectrometer CCD, when the FTP was immersed in 10 mM Phosphate Buffer Saline (PBS), pH 7.4. A spectrum profile analysis was performed by binning a few pixels around the bright spot, in order to increase the signal-to-noise ratio. By fitting resonance spectrum with the Lorentzian profile, it was found that the LSPR resonance of this gold nanorod was 729 nm, with a quality factor of 10.

FIG. 1 shows an example of a gold nanorod Fiber tip probe (FTP). FIG. 1A is a Scanning Electron Microscope (SEM) image of a FTP. The optical fiber gradually tapers from 125 micrometers to below 100 nm. FIG. 1B is an enlarged SEM image of an end of a FTP showing a single nanorod immobilized on the FTP. FIG. 1C show optical images of the LSPR FTP with the excitation light source off (left) and on (right) in air. A dot (right image) corresponds to the LSPR of a gold nanorod. In this experiment, white-light from a halogen source was coupled into the fiber and used to excite the gold nanorod at the fiber tip. FIG. 1D is an image from the spectrometer CCD at the zeroth order grating. FIG. 1E shows an LSPR spectrum at the first order grating (right). This FTP was immersed in 10 mM phosphate buffered saline (PBS).

Example 2

Figure 2A:
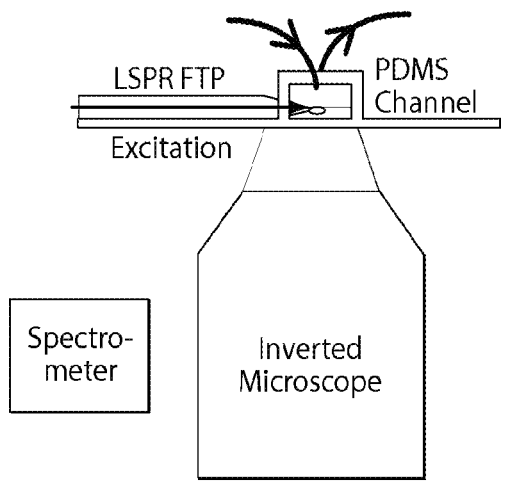
FIGS. 2A-2D illustrate localized surface plasmon resonance using various members, in accordance with one embodiment of the invention.
Figure 2B:
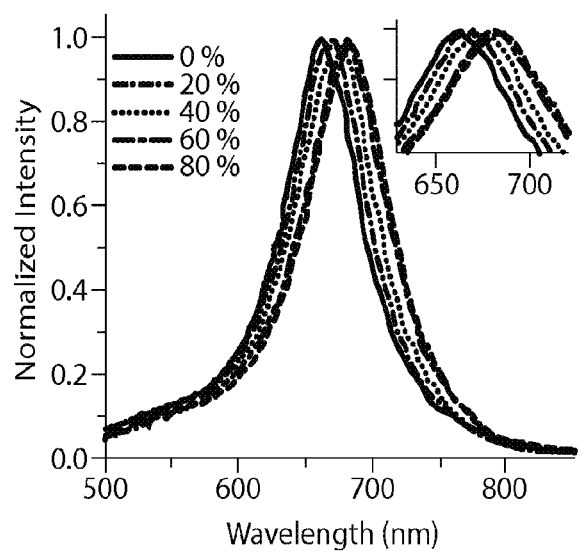
Figure 2C:
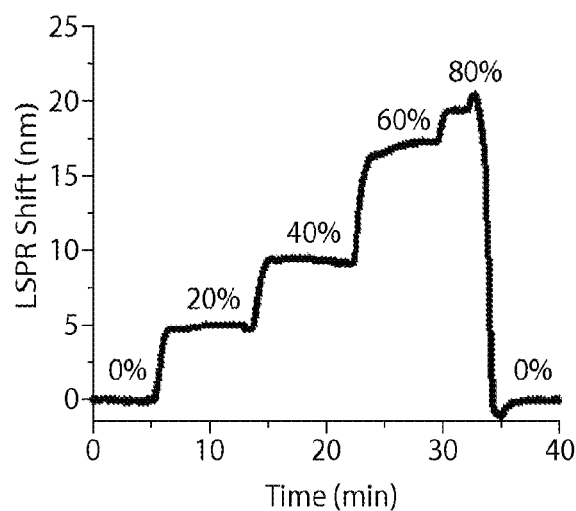
Figure 2D:
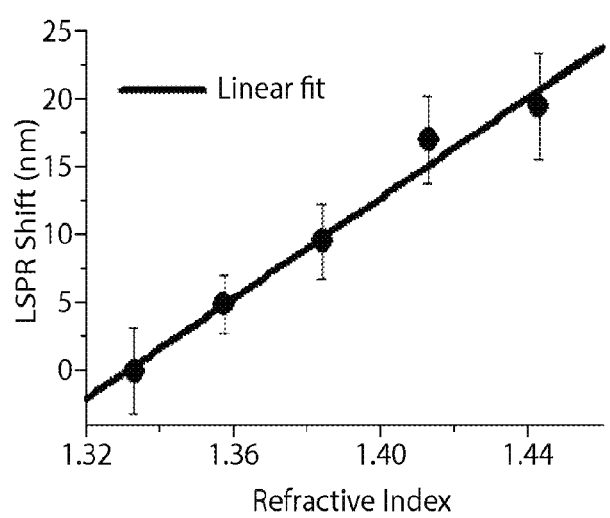

To test for sensitivity, an LSPR-FTP probe was characterized in an in vitro aqueous environment in this example. First, the FTP was used to detect different concentrations of glycerol in water. Solutions of 20%, 40%, 60%, and 80% of glycerol in water were prepared and injected into a microfluidic channel. The FTP was inserted into the channel, and sealed with epoxy. The LSPR signal excited through the fiber coupled with halogen light source was monitored with inverted microscope (Olympus IX71) (FIG. 2A). FIG. 2B shows representative spectra for each concentration. FIG. 2C shows the real-time measurement of the LSPR peak wavelength (from Lorentzian fitting). Steps in the figure indicate the time when concentration of solutions was changed. FIG. 2D shows the resonance wavelength vs. refractive index of the solution. The LSPR shifts to longer wavelength, as expected, when the concentration of the glycerol was increased, due to increase in the refractive index of the solution. The bulk index sensitivity of the FTP can be defined as the resonance shift per unit refractive index change in the surrounding medium. It was found that the sensitivity of this device was 187+/−25 nm/RIU (repeated for five times), significantly greater than that of the 39 nm diameter gold spheres (80 nm/RIU). Gold nanorods were also advantageous over gold spheres because of the reduced damping loss (thus higher Q-factor), which is important for resolving the resonance shift.

FIG. 2 shows in vitro characterization of the LSPR FTP used in this example. FIG. 2A shows a schematic of a setup for in vitro characterization of the LSPR FTP. The FTP sensor was assembled in a homemade PDMS fluidic channel. The LSPR signal excited through the fiber was collected via an inverted microscope, and analyzed by a spectrometer. FIG. 2B shows a normalized LSPR signal in various glycerol/water concentrations. The inset shows a zoomed-in view of the LSPR peaks. FIG. 2C shows real-time monitoring of the LSPR when different concentrations of solutions were injected in the channel. The resonance wavelength was obtained by fitting LSPR signals to the Lorentzian equation. FIG. 2D shows the dependence of the LSPR position on the refractive indices of the solvents. The error bar is from the measurements of five different nanorods. A bulk index sensitivity of 187+/−25 nm/RIU was obtained from linear fitting.

Example 3

Figure 3A:
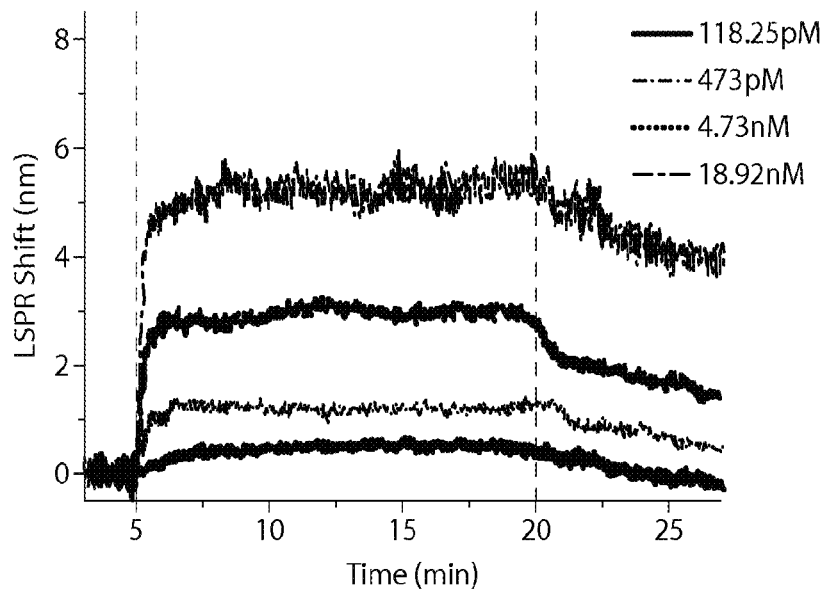
FIGS. 3A-3C illustrate localized surface plasmon resonance using various members under physiological conditions, in another embodiment of the invention.
Figure 3B:
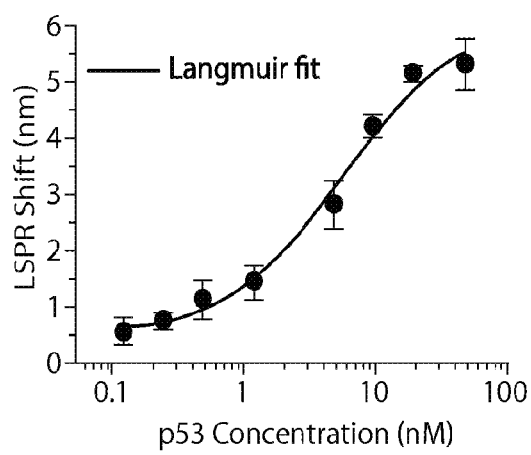

An FTP was used in this example to detect different concentrations of proteins in PBS solution. The gold nanorod on the tip of the FTP was functionalized with a p53 antibody (Santa Cruz sc-126). Different concentrations of p53 (Santa Cruz sc-4246) in PBS were injected into the fluidic channel for 15 minutes, followed by washing with pure PBS. FIG. 3A shows the real-time response at several representative concentrations. An LSPR shift of 5.13 nm was observed upon introducing 18.92 nM p53 solution. After washing with pure PBS at 20 minutes, the resonance decreased slowly, indicating the dissociation kinetics. A LSPR shift of 0.55 nm was observed from 1 nM p53 solution. The minimum discernible wavelength shift was ~0.3 nm, estimated from the LSPR response to pure PBS flowed for the first five minutes (black dashed line in FIG. 3A). The LSPR shift vs. concentrations is shown in FIG. 3B, and fitted with Langmuir equation. The dissociation constant of p53 from anti-p53 was 5.5 nM.

Figure 3C:
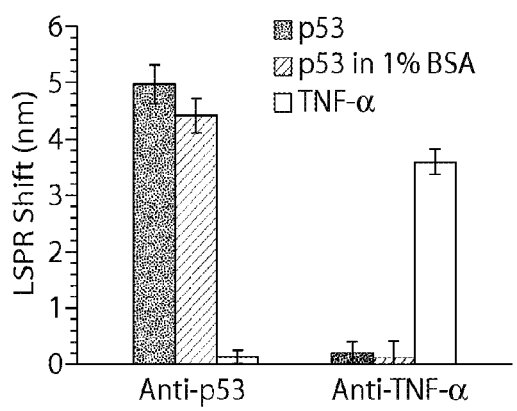

To study the specificity of the system, various FTPs were functionalized with antibodies of either tumor suppressor p53 or tumor necrosis factor (TNF-α, TNF-alpha), and these were used FTPs to detect p53 and TNF-alpha (FIG. 3C). When the FTP was functionalized with anti-p53, it could detect p53 both in pure PBS and in PBS with concentrated Bovine Serum Albumin (1% BSA) as background. On the other hand, the sensor was not sensitive to TNF-alpha, a mismatched antigen-antibody pair. A FTP functionalized with anti-TNF-alpha also showed high specificity to TNF-alpha only (FIG. 3C). This demonstrated that the LSPR FTP showed high specificity to the targeted protein and non-specificity to the other proteins. Because the LSPR of the nanorod had an exceptionally smaller optical mode volume (on the order of the physical dimension of the nanorod) than other optical resonators, the sensor was sensitive to only a few nanometers from its surface and was insensitive to untargeted proteins.

FIG. 3 shows in vitro characterization of the LSPR FTP in physiological conditions in this example. FIG. 3A shows real-time measurement of LSPR shifts at various p53 concentrations. In all cases, the blank PBS was injected into the fluidic channel for the first 5 minutes (before the left dashed line). Different concentrations of p53 in PBS were injected into the channel for 15 minutes, followed by an additional PBS wash step to observe dissociation of p53 from its antibody (after the right dashed line). FIG. 3B shows the LSPR shift vs. p53 concentration. A binding affinity of 5.4 nM was extracted from fitting with the Langmuir equation. Three repeated experiments were performed. FIG. 3C shows a specificity test of the LSPR FTP sensor. The LSPR FTPs were coated with anti-p53 and anti-TNF-alpha respectively, and both sensors were used to detect p53, p53 in 1% BSA, and TNF-alpha. The LSPR shift signal occurred in cases where coated antibodies were paired correctly with their antigens, thus demonstrating high sensor specificity. High specificity was retained when the p53 antigens were in a high background of BSA.

Example 4

Figure 4B:
Figure 4C:
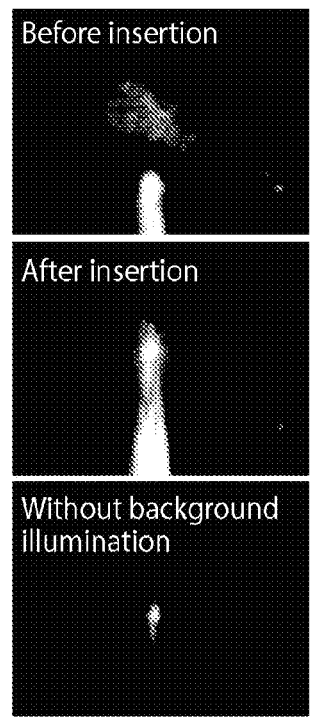

An FTP may offer a unique three-dimensional nanoscale form-factor in accordance with certain embodiments; thus, it may be used, for example, as a minimally invasive bioprobe into cells. This example demonstrates how p53 in HeLa cells dynamically reacted to ultra-violet (UV) exposure and neocarzinostatin (NCS) drug treatment. A commercial anti-p53 to intracellular p53 was first validated by performing western blotting with HeLa cell lysis (FIG. 4B). In order to minimize the invasiveness to the cell, an anti-p53 functionalized FTP was inserted in and retracted out of the cell every 30 minutes. During each measurement, the FTP was first into the cytoplasm of the cell, incubated for 5 minutes, then the FTP was retrieved out of the cell, and its LSPR was measured in the cell culture medium adjacent to the cell of interest. This process was conducted to minimize the scattering background from the cytoplasm when FTP was inside the cell, as well as to wash off the non-specific bindings of other proteins inside the cell. The LSPR measurements were immediately taken after the retraction, to prevent unbinding of p53 from anti-p53. After the FTP was inserted into the cell, a single gold nanorod glowing could be observed inside the cell and gradually dimming down after a few minutes (FIG. 4C). This dimming behavior was attributed to the scattering background from the possible non-specific binding of cytoplasmic proteins onto the nanosize tip, and can serve as an indication that FTP is in the cytoplasm.

Figure 4D:
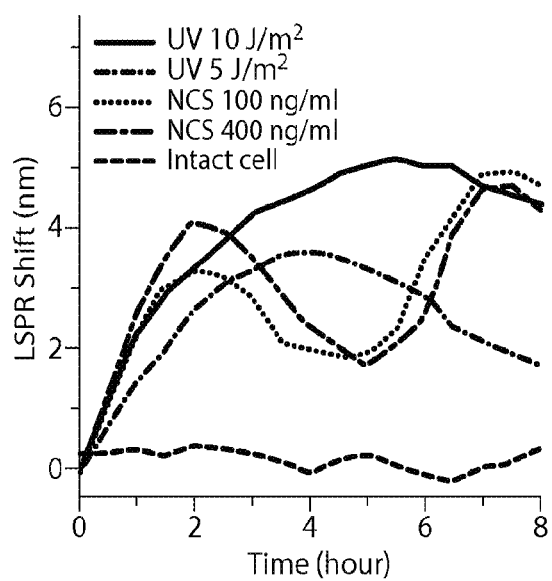
Figure 4E:
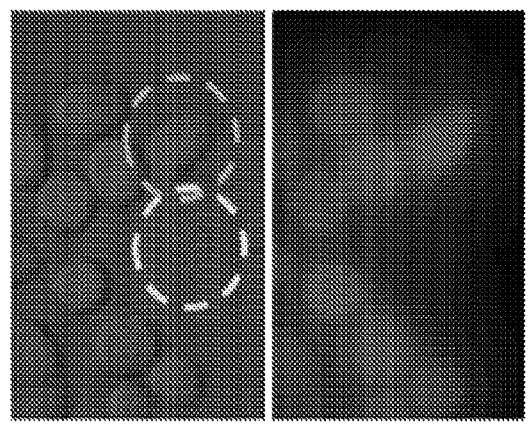

The intensity of UV light source was first calibrated. Live HeLa cells were exposed by different dosage of UV light or different concentrations of NCS. FTP experiments were performed immediately after the treatments. The results of these experiment indicated that different stresses triggered different temporal response of p53. As shown in FIG. 4D, the dynamics of p53 could be quantified in individual cells in response to UV and a sustained increase in amplitude and duration in proportion to the UV dose could be observed. This dose-dependent, sustained increase of p53 in response to UV is in clear contrast to the repeated pulses in response to NCS. The amplitude and duration of individual p53 pulses did not depend on the NCS dose.

As a control experiment, the same procedure was performed on an intact HeLa cell. As shown in FIG. 4D, the intracellular p53 level remained constant. This consistency also indicated that the FTP was minimally invasive and had little effect on the cell physiology. In order to further confirm that the HeLa cell was alive after a series of measurement (8 hours long), a fluorometric assay of calcein was used (Invitrogen LIVE/DEAD). These results agree with previous studies of p53 using fluorescent microscopy and western blotting.

FIG. 4 shows intracellular p53 detection in a single living HeLa cell with FTP. FIG. 4A is a schematic set-up of the FTP system used in this example. The probe in this example included a nanorod immobilized on the sub-100 nm tapered tip of an optical fiber, inserted into a single living cell at designated positions using a three-axis micromanipulator. FIG. 4B shows an immunoblot of commercial p53 and intracellular p53 in HeLa cell lysis. Commercial anti-p53 paired well with commercial and intracellular p53. FIG. 4C shows a sequence of EMCCD images of a FTP penetrating a single HeLa cell, viewed from below. The FTP was first positioned outside the cell with its tip lying slightly flat against the petri dish substrate. It was then punctured into the side of the cell. Without background illumination, the LSPR signal could be seen from the nanorod glowing inside the cell. FIG. 4D shows p53 dynamics in intact, UV exposed and NCS treated HeLa cells. The p53 showed sustained concentration increases under UV, and pulsed oscillation under NCS. FIG. 4E shows phase-contrast and fluorescent image of cells that have been punctured by FTP. A cell in the upper circle fluoresced after treatment with calcein viability dye, and thus was alive after a series of measurement (8 hours long) with the FTP. The cell showed similar levels of green fluorescence intensity indicating the viability of both poked and intact cells. However, a cell in the lower circle was dead after being punctured once by a FTP with 5-micrometer tip in diameter.

FTP probes such as those discussed in this example may offer certain advantages. First, this is a label-free technology, e.g., free from labels interfering with proteins. Second, the FTP was capable of interrogating single cells, free from cell harvest and cell lysis. Third, the FTP revealed real-time dynamics, and was quantitative. For example, by referring to measurements in the in vitro environment, the p53 concentration could be inferred up to the order of 10 nM under external stress (UV illumination).

Combining the advantages of high selectivity from antibody-antigen recognition and high sensitivity of LSPR, this example demonstrated a novel three-dimensional nanoscale bioprobe for intracellular protein detection. This method may be especially useful for cells and systems that are hard to label, for example, immune cells, neurons, and precious patients' cells and circumstances that require in vivo and in situ detection. While this example uses s a single bioprobe detecting one specific protein in single cells, these approaches may be extended to other systems, e.g., high-throughput multiplexed system, for instance, by using fiber arrays or nanowire arrays.

Example 5

This example describes, in additional detail, certain procedures used in the above examples.

Figure 5A:
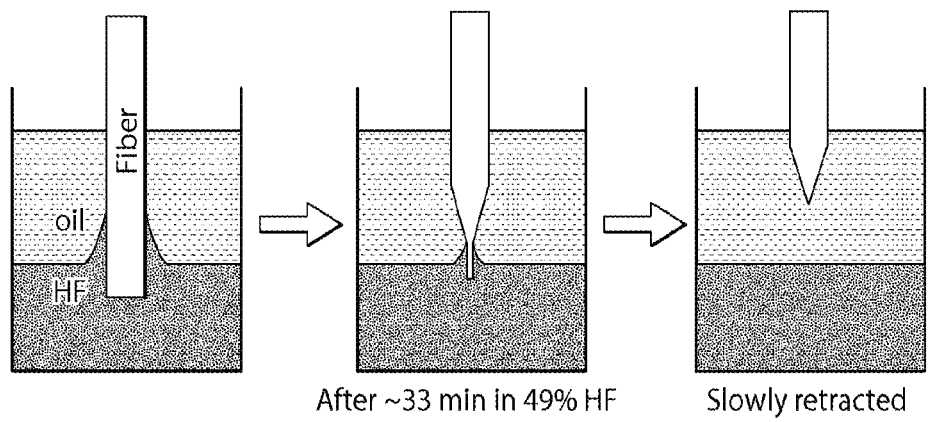
FIGS. 5A-5D illustrate the etching of a member, according to certain embodiments of the invention.
Figure 5B:
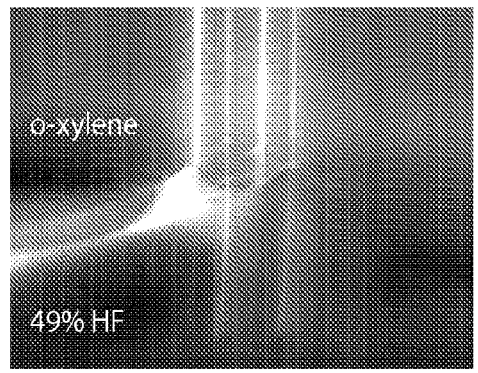
Figure 5C:
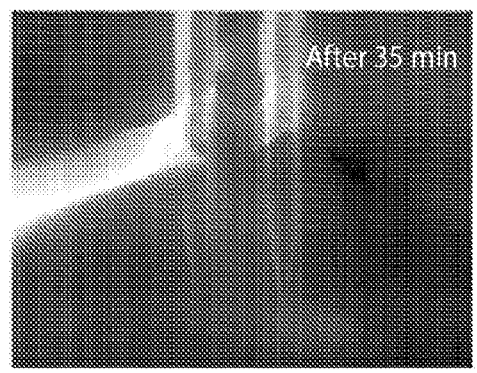
Figure 5D:
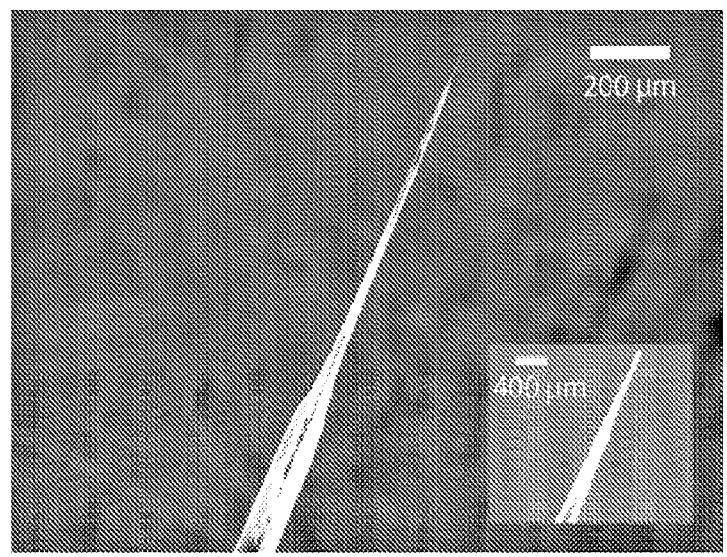

Fabrication of an FTP. The Fiber Tip Probe (FTP) was fabricated from the widely available glass optical fibers. Glass fibers (SM28, Thorlabs Inc.) were etched with hydrogen fluoride (HF) wet chemistry to taper the tip down to sub-100 nm sizes (FIG. 5). First, the acrylate coating layers of the optical fibers were removed for a length of 10 mm. Then, the stripped parts were immersed in the piranha solution ($H_2SO_4$:$H_2O_2$ of 3:1) for 10 min for cleaning. The fibers were then cleaved to generate flat facets. A fiber holder that could hold as many as 10 fibers was mounted on a translational stage. The cleaved fibers were perpendicularly dipped into the HF/o-xylene interface, roughly 1 mm deep into HF. The HF wetted the fiber surface with an initial meniscus height (FIG. 5A). The fiber tip was sharpened by the gradual reduction of the etchant meniscus height that was associated with the decrease of the tip diameter during etching. In order to prevent disturbances of the etching rate and maintain smoothness to the end of the nano-tip, the etching apparatus was placed on the air-floating optical bench and in a windproof enclosure. The whole etching process could be monitored with a camera (FIG. 5B). After 35 min, the fibers were first taken out of HF/o-xylene and rinsed immediately with de-ionized water in order to prevent further etching by residual HF. To further fine-tune the tip size, the HF was replaced with Buffered Oxide Etch (BOE 5:1), as BOE had an etch rate $1/10^{th}$ of HF. The etching time in BOE was precisely controlled, and fiber was monitored under the microscope, and compared to an image of fibers with known sizes under an optical microscope. As shown in FIGS. 1D and 5C, sub-100 nm tip sizes were achieved.

FIG. 5 shows the HF wet-etching process used in this example. FIG. 5A shows schematics of the etching procedures. First, the fiber was immersed in the HF/o-xylene interface for 33 minutes. After the fiber was etched to sub-micron sizes, the fiber was slowly retracted out to create a nanosize tip, a few micrometer in length and sub-100 nm in diameter. FIGS. 5B and 5C show microscope images of two fibers before and after etching. After 35 minutes of etching, a clear cone shape at the fiber tips could be seen. FIG. 5D shows an SEM image of the fiber etched to form two cone shapes. The inset figure shows a magnified SEM image of the FTP tip, showing that the fiber tip in this example had a diameter of ~85 nm.

Preparation of MUA-coated gold nanorods. 100 microliters of a 20 mM solution of 11-mercaptoundecanoic acid (11-MUA, Sigma-Aldrich) prepared in ethanol was mixed with 1 mL of cetrimonium bromide (CTAB) capped gold nanorods (Nanopartz Inc.). The mixed solution was sonicated for 90 minutes at 55° C. After keeping the mixed solution at room temperature overnight, sedimentation of the rods was observed. The nanorods were re-immersed in a sonic bath and then the excess MUA was removed using centrifugation at 7000 rpm for 10 minutes. Then, MUA-coated gold nanorods could be readily redispersed in $H_2O$. These nanorods were dispersed on a thin cover glass and one nanorod was picked up by FTP mounted on the micromanipulator (FIG. 6).

Figure 6A:
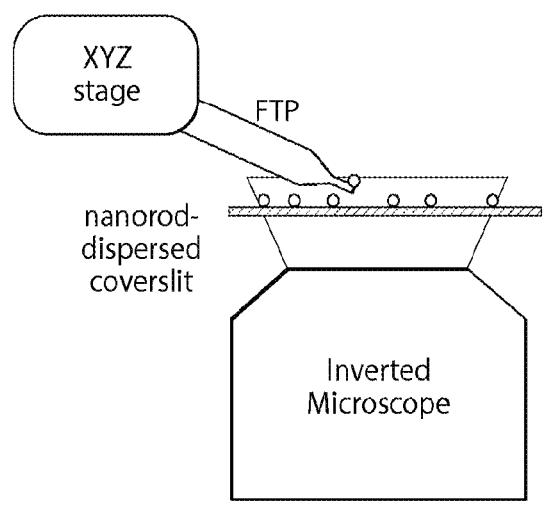
FIGS. 6A-6D illustrate the conjugation of a gold nanorod to a member, in another embodiment of the invention.
Figure 6B:
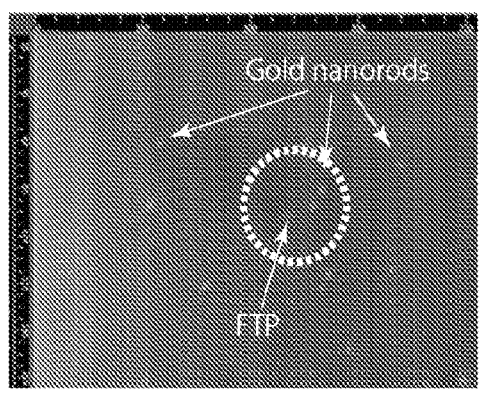
Figure 6C:
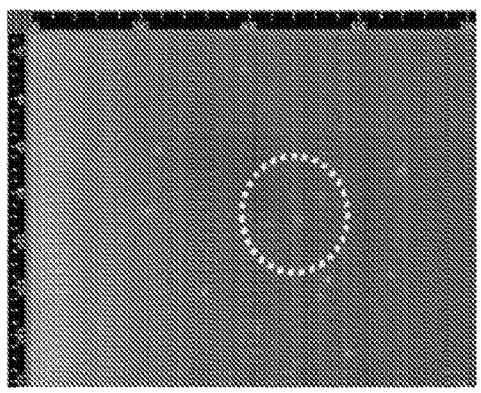
Figure 6D:
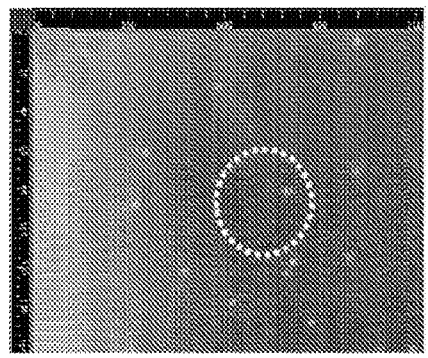

Conjugate gold nanorod on FTP. A single gold nanorod was conjugated on the sub-100 nm tip of the FTP as follows. The gold nanorods coated with 11-MUA were first dispersed onto a cover-glass and could be observed under dark field (FIGS. 6B-6D). The FTP was then dipped into optical adhesive (Norland NOA 138) for a few seconds and immediately mounted onto the micro-manipulator. The FTP precisely moved to the top of a single gold nanorod, and picked up the gold nanorod before the adhesive dried up. The pig-tailed end of the FTP was then connected to a halogen lamp, whose UV components cure the optical adhesive.

FIG. 6 shows an example of FTP conjugation with a single gold nanorod. FIG. 6A shows an experimental setup for picking up a single nanoparticle from the cover glass. FIGS. 6B-6D are EMCCD images from scattered light collected through the objective lens during the pick-up process of a single nanoparticle from the surface by a FTP. The circled area is a target region with a FTP (indicated with lower arrow) approaching to pick up one of individual nanorods (indicated with upper arrows). The tip applied a shear force onto the surface (FIG. 6B), established contact with one particle (FIG. 6C), and was conjugated with a nanorod and was retracted from the surface (FIG. 6D).

Localized Surface Plasmon Resonance (LSPR) measurement. To study the effect of orientation to the LSPR of the gold nanorod, two nanorods were attached that were coincidently arranged perpendicular to each other (FIG. 7A). The strong emission of the gold nanorod was along its longuitudinal axis. Therefore, a linear polarizer could be used to selectively collect the emission from each nanorod, as shown in FIG. 7B. Spectrum analysis was further done by binning around the bright spot to maximize the signal-to-noise ratio. It was observed that LSPR peaks from both nanorods were respectively at ~700 nm, but different by 50 nm. This was in consistent with the previous study of polarization dependence of the gold nanorod spectrum.

FIG. 7 shows the gold nanorod (GNR) SPR polarization test. FIG. 7A is an SEM image of the Plasmonic FTP with two nanorods glued perpendicularly to each other. FIG. 7B is an EMCCD image at two different excitation polarization. Each nanorod glowed at different polarizations. FIG. 7C shows SPR peaks of the two nanorods obtained after binning a few pixels around each nanorod with EMCCD specrtrometer.

Fabrication of PDMS channel. SU-8 (Shipley) was used to pattern a 150 micrometer thick mold on top of a silicon substrate via photo-lithography. A 125 micrometer-wide channel was fabricated in the middle of the flow channel (2 mm by 10 mm) so that the fiber (125 micrometers in diameter at its stem) had room to reside in the middle of the flow channel. The FTP was pasted onto an $O_2$-cleaned glass slide and the PDMS channel was carefully assembled onto the glass slide.

Surface functionalization for in vitro test. 100 mM EDC (Sigma-Aldrich) and 100 nM anti-p53 (Santa Cruz) in 10 mM PBS was flowed into the PDMS channel for 1 hour. EDC molecules reacted to the carboxyl group of MUA molecules, which capped the gold nanorod, and form unstable esters, which reacted to the amine groups on the antibodies. The channel was then flushed with PBS 1× for 30 min to get rid of excess non-specifically bound anti-p53. The FTP was then flowed with various concentrations of p53 for in vitro characterization.

Verification of surface functionalization with UV-Visible spectroscopy. The above surface functionalization procedure was verified using UV-Visible spectrometer (Jasco Inc.). The change of the absorption spectra was measured at each step of the functionalization procedure. First, MUA-capped nanorods were mixed with 100 mM EDC (Sigma-Aldrich) and 100 nM p53 antibody (Santa Cruz) in PBS 1× (pH 7.4) for 1 hour. The resulting nanorods were then collected by centrifugation at 5000 rpm for 5 min and resuspended in a buffer containing 5 mM CTAB. After three rounds of vigorous washing, the collected nanorods were sonicated in 5 mM CTAB solution for 10 minutes. As shown in FIG. 8B, after the 11-MUA coating, a red-shift of 5-7 nm in the longitudinal peaks was clearly identifiable, indicating the alkanethiol self-assembled-monolayer (SAM) formation. A further red-shift of the surface plasmon resonance peak was observed due to the antibody functionalization.

Different concentrations of p53 protein were added to the anti-p53 modified gold nanorod solution. Each solution was vortexed for 5 min under room temperature before UV-Visible spectrum measurements. In order to minimize bulk refractive index change by the addition of protein solution into the nanorod solution, a small volume of p53 protein was used from the original p53 stock solution with a high density of proteins (50 micrograms/ml). ~1 microliter of the p53 stock solution was added to 1 ml of gold nanorods to obtain 1 nM p53. Also, the concentration of p53 was ensured to be sufficiently higher than that of nanorods; the nanorod solution was ~$10^{10}$ ml$^{-1}$, while 1 nM p53 was ~$10^{12}$ ml$^{-1}$.

Figure 8A:
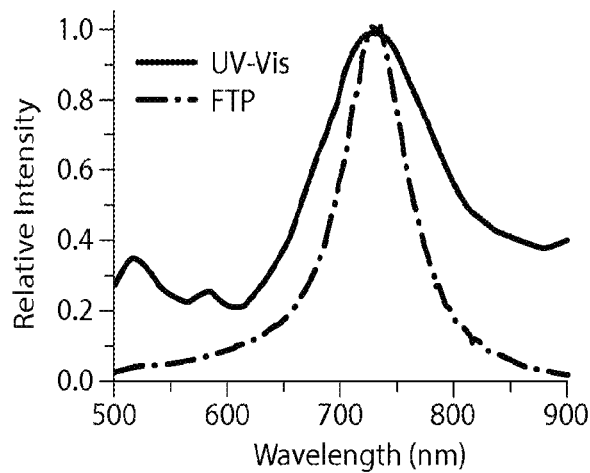
FIGS. 8A-8C illustrate spectral profiles of gold nanorods, in still another embodiment of the invention.
Figure 8B:
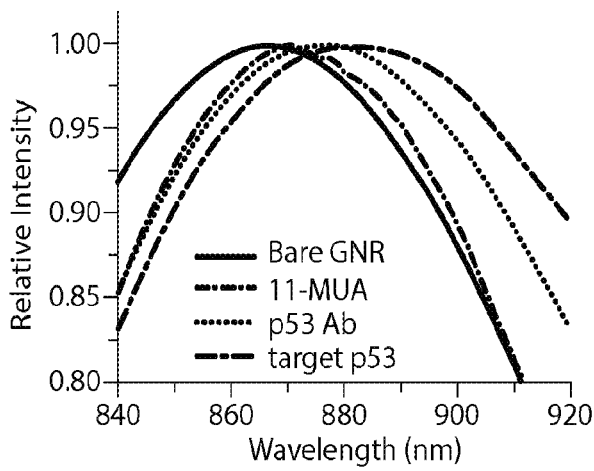
Figure 8C:
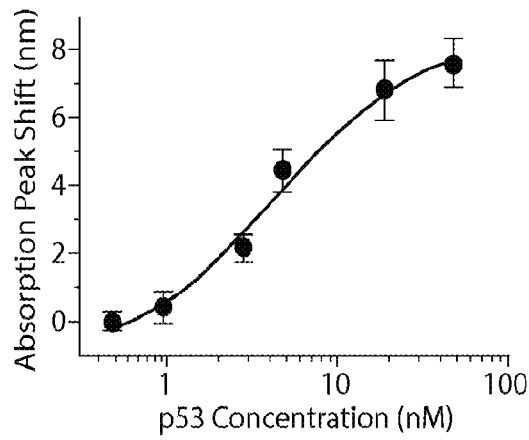

FIG. 8C shows the resonance shift vs. p53 concentration. The fitted curve uses the Langmuir equation. The affinity of $K_D$=4.3 nM was obtained from fitting. It can be noted that the resonance spectrum from UV-visible spectrometer was an ensemble measurement from the gold nanorod solution, and thus showed inhomogeneous broadening than the spectrum obtained from the single nanorod that was attached to the FTP (FIG. 8A).

FIG. 8 thus shows characterization of surface functionalization with UV-Vis Spectrometer. FIG. 8A shows scattering spectra of a single gold nanorod on a glass substrate (lower curve) measured via EMCCD spectrometer and the extinction spectrum of an ensemble of gold nanorods measured via UV-Vis spectrometer (upper curve). The ensemble spectrum from nanoparticles with a distribution of size and shapes exhibited heterogeneous broadening compared to the single Lorentzian peak observed from each resonance of a single nanoparticle. FIG. 8B shows UV-Vis absorption spectra of gold nanorods at each functionalization step. Functionalization of GNRs introduces a red-shift in the longitudinal plasmon peak. FIG. 8C shows a binding curve of p53 obtained from UV-Vis Spectrum analysis. The error bar is from analysis of three experiments.

Figure 9A:
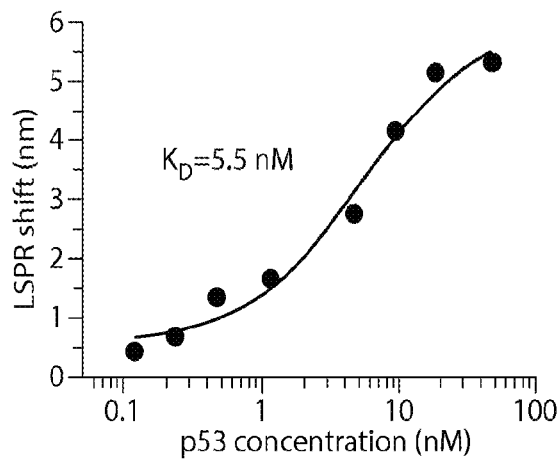
FIGS. 9A-9C illustrate binding of p53, according to one embodiment of the invention.
Figure 9B:
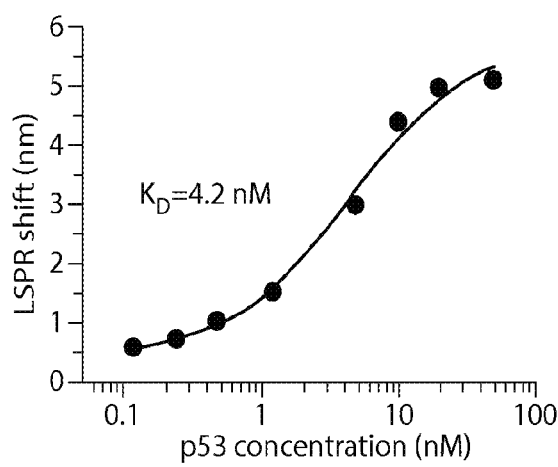
Figure 9C:
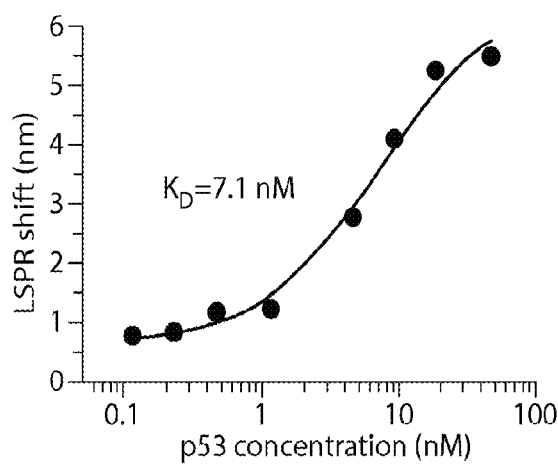

In vitro p53 detection. Repeated experiments were performed for in vitro detection. The FTP was functionalized with anti-p53 (Santa Cruz). Different concentrations of p53 (Santa Cruz) in PBS were injected into the PDMS channel for 15 minutes, followed by washing with pure PBS. FIG. 9 shows the LSPR shifts vs. concentration of p53, measured with three different FTP devices. Langmuir fitting was performed, and the affinity of p53 to anti-p53 was measured to be 5.5 nM, 4.2 nM and 7.1 nM, respectively. The variance characterized the discrepancy between devices, including size difference of nanorods and difference in the chemical functionalization. In FIG. 9, showing the binding curves of p53 obtained from in vitro characterization and LSPR shift vs. p53 concentration, three curves were obtained from three different FTP samples.

Figure 10A:
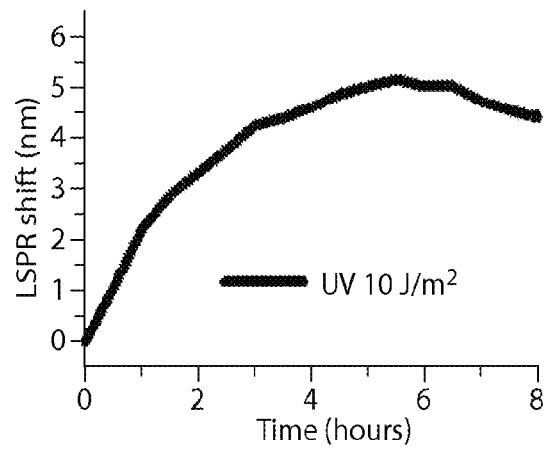
FIGS. 10A-10F illustrate p53 dynamics within a cell, in another embodiment of the invention.
Figure 10B:
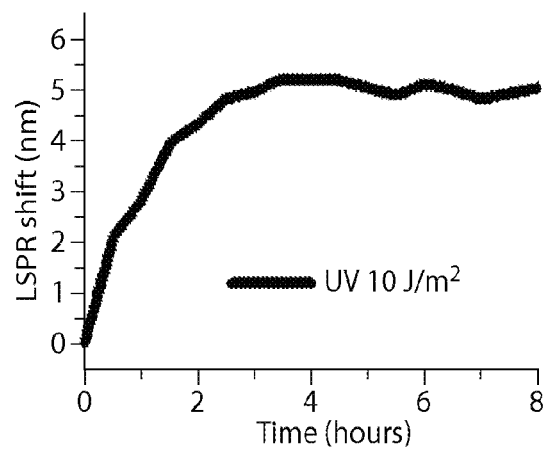
Figure 10C:
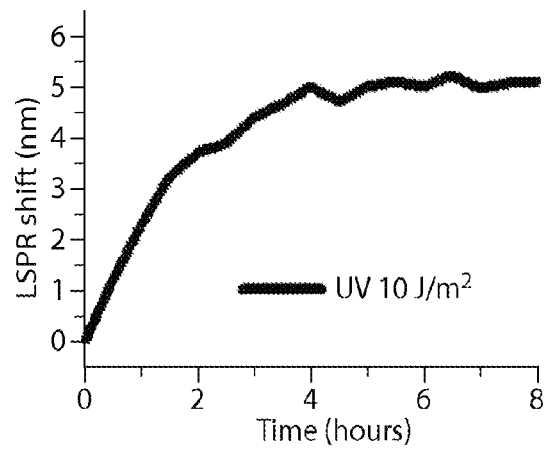
Figure 10D:
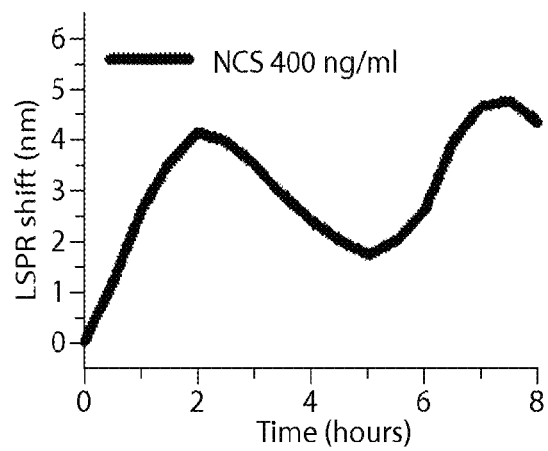
Figure 10E:
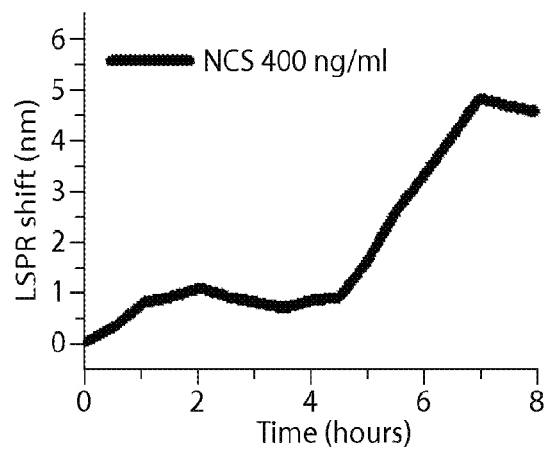
Figure 10F:
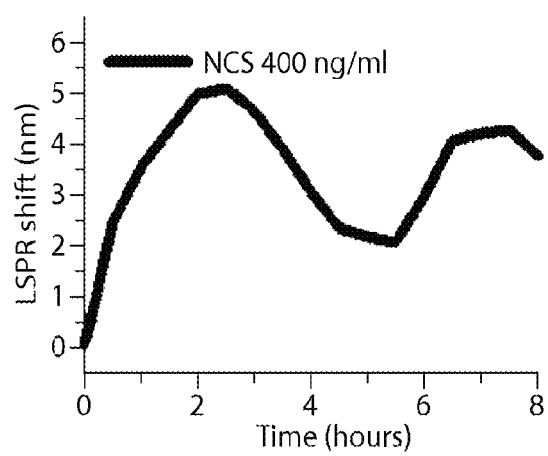

Intracellular p53 detection. Repeated experiments were performed to demonstrate intracellular p53 detection. An FTP was functionalized with anti-p53. HeLa cells were either exposed to 10 J/m$^2$ of ultra-violet (UV) light, or treated by 400 ng/ml of NCS drug. The FTP was inserted into the cytoplasm of the cell, incubated for 5 minutes, and then retrieved from the cell and measured in the cell culture medium. This insertion, incubation, and measurement were repeated every 30 minutes. Different FTPs were used in each experiment. FIGS. 10A-10C show the p53 response to UV exposure. Its concentration increased with time and plateaued after about 4-5 hours. FIGS. 10D-10F show the p53 response to NCS drug. In contrast, the p53 concentration showed repeated pulse behavior.

Cell culture and immunoblots. Human cervix epithelial HeLa cells (American Type Culture Collection, ATCC) were cultured at 37° C. in DMEM F-12 Medium supplemented with 10% fetal calf serum, 100 U/ml penicillin, and 100 mg/ml streptomycin.

The cells were harvested, lysed, and the total protein concentration was measured (10 mg/mL) by a Bradford assay (Thermo Scintific). The proteins were then separated by electrophoresis on 4-20% Mini-PROTEAN TGX Stain-Free precast gels (Bio-Rad), and transferred to PVDF-membrane (Bio-Rad) by electroblotting. The membrane was incubated with primary p53 monoclonal antibody (Santa Cruz) overnight, washed, and incubated with secondary antibody for 2 hours. Protein levels were then observed by chemoluminiscence after adding SuperSignal West Pico Working Solution (Thermo Scientific) for 5 minutes. Both commercial p53 and lysate of HeLa cells paired well to the commercial anti-p53.

Cell viability test. A fluorometric assay of calcein AM was used, following the suggested protocol (Invitrogen LIVE/DEAD). The cells were probed or loaded, and the positions of those cells were documented by carving out reference marks in the Petri dish using a broken FTP after the experiment. The cells were then incubated for 6 hours, after which they were treated with 2 micromolar of calcein AM in PBS. Fluorescence images were captured with a Nikon Eclipse Ti fluorescence microscope with a LED laser (Thorlabs).

Example 6

This example describes a fiber tip probe (FTP) system having a nano-diamond sensor. As shown in this example, the sensor may be used for applications such as electric field, magnetic field, or temperature detection.

Figure 13A:
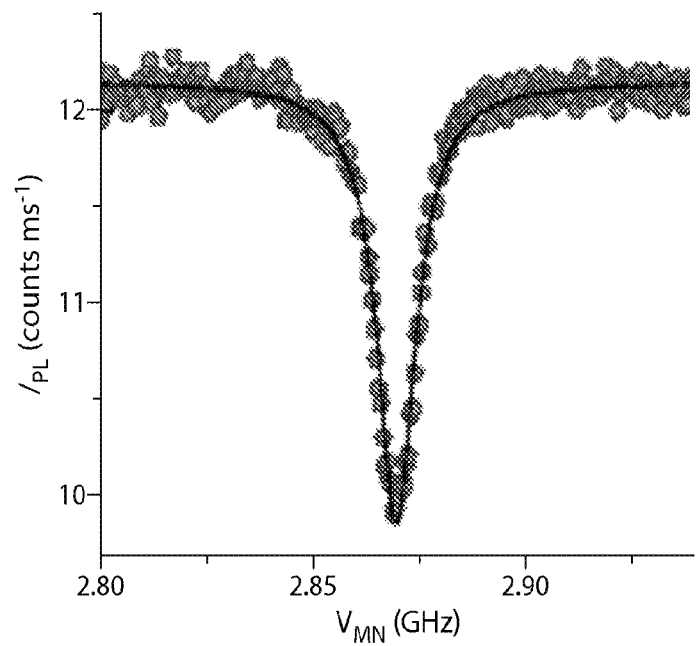
FIGS. 13A-13B illustrate the use of a nano-diamond particle to detect electrical stimuli, in one embodiment of the invention.
Figure 13B:
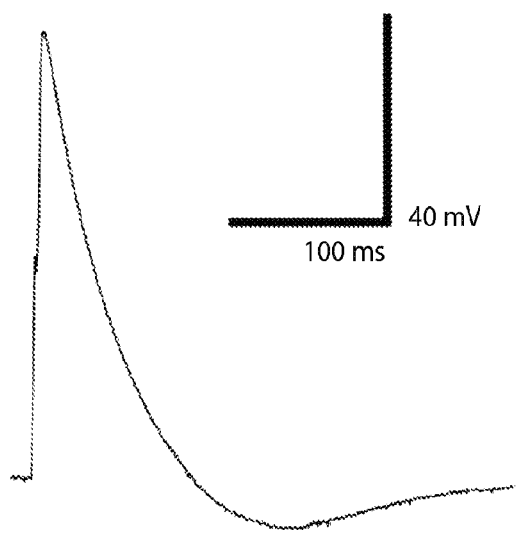

Diamonds may have a nitrogen vacancy (NV) center, composed of one substitutional nitrogen atom and an adjacent vacancy. The NV may form a ground state spin triplet that can be controlled coherently at room temperature using electromagnetic fields and temperature. NV centers can be excited by an off-resonant 532 nm laser, and subsequently may emit fluorescence with a 637 nm zero-phonon line. The state $m_s=-1$ can be isolated from the state $m_s=+1$ by applying an external magnetic field to induce Zeeman splitting; electric field and temperature shifts $m_s=0$. The ground-state spin splitting around 2.88 GHz, or electron spin resonance dip (FIG. 13A), either shifts or splits, depending on which external stimuli had been applied. For instance, FIG. 13B shows an FTP having a nano-diamond immobilized at an end that is inserted into a cardiomyocyte cell or a neuron to measure its intracellular action potential.

Example 7

This example describes, in additional detail, the FTP functioning as a mechanical sensor, in accordance with certain embodiments of the invention.

Figure 14A:
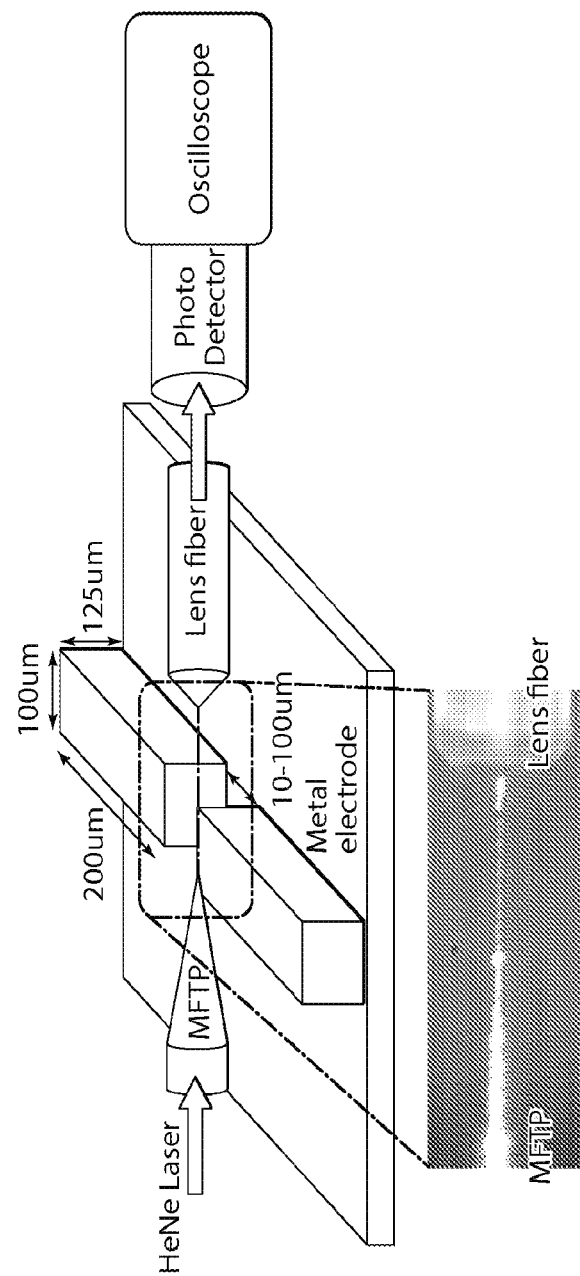
FIG. 14A-14B illustrate the determination of mechanical stimuli, in another embodiment of the invention.

FIG. 14A shows the experimental setup of the device used in this particular example. A mechanical FTP is placed perpendicular to a gap between two electrodes, which are spaced 10 to 100 micrometers away. AC voltage (up to 200 V) is applied between the two electrodes and oscillates the fiber at the AC frequency. A HeNe laser is coupled to the FTP, and the lens fiber (NA=0.7, Thorlab) arranged parallel to the tip of the FTP will collect the transmitted light. As the AC modulating frequency reaches the mechanical mode of the FTP, the fiber will oscillate with large amplitude, and the collected light through the fiber will measure higher peak-to-peak variations in the transmitted light.

Figure 14B:
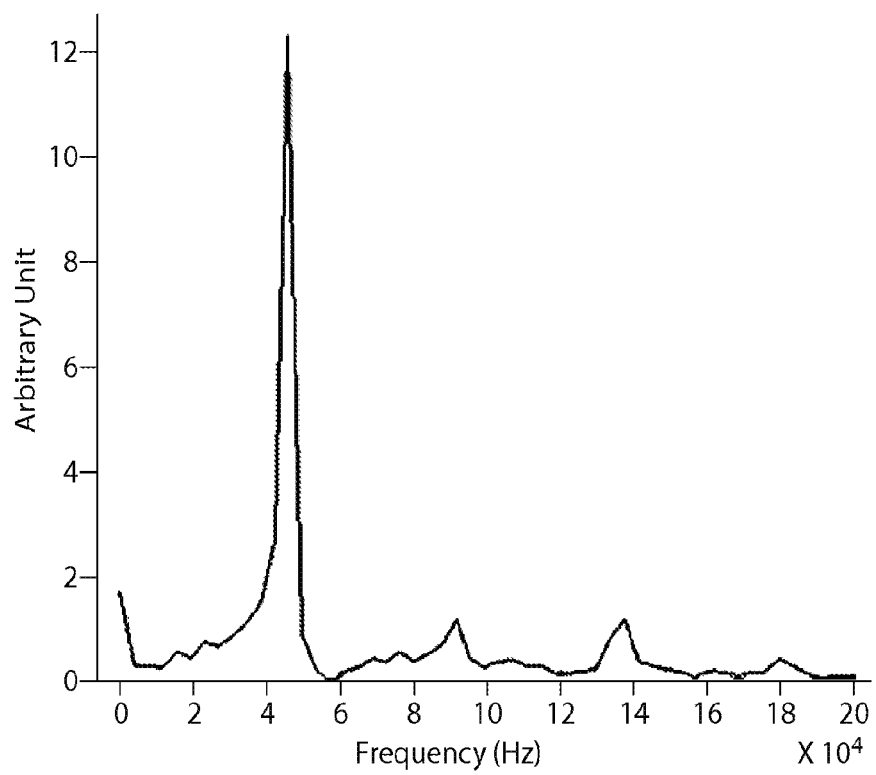

By scanning the AC modulation frequency and analyzing the Fast Fourier Transform (FFT) of the transmitted light through the lens fiber, the resonance frequency of the FTP can be determined. For instance, as is shown in FIG. 14B, a modulation at 20 kHz resulted in resonantly enhanced vibrations at 22.8 kHz.

This mechanical resonance frequency of the fiber may be very sensitive to the mechanical alternation to the fiber. For example, the end portion of the FTP may be coated with an antibody for detection of a protein or other antigen, platinum for detection of hydrogen, or a hydrogel for detection of water (e.g., to determine humidity).

Example 8

This example shows FTP functioning as an optical guide to characterize micro- to nano-optical devices, in another embodiment of the invention.

Figure 15A:
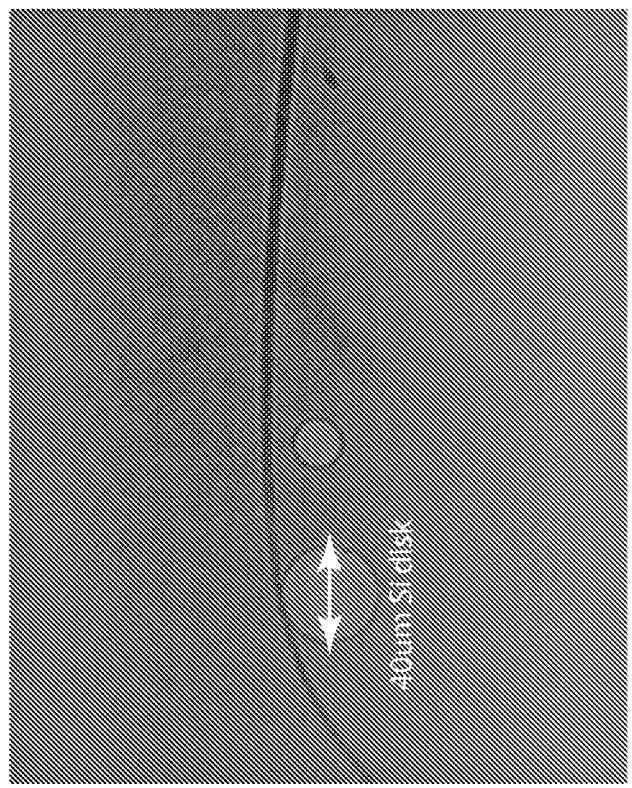

Thin nanowire portion of single-ended or double ended FTPs (FIGS. 1F, 1G, 1H, and 1I) can approach optical devices and couple light through them. As shown in FIG. 15A, a micrometer-thick double-ended fiber approached a silicon disk with 40 micrometer in diameter and coupled light through it. On one end of the fiber, a 1550 nm laser was coupled, and on the other end, the laser light was collected and analyzed. As shown in FIGS. 15B and 15C, periodic resonance features in the spectrum could be observed. This showed that the fiber could function as a optical waveguide to couple light into the FTP. Any frequencies may be used, including telecom wavelengths or visible wavelengths.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

When the word "about" is used herein in reference to a number, it should be understood that still another embodiment of the invention includes that number not modified by the presence of the word "about."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article for inserting a particle into a cell, the article comprising:
   a member configured to guide and/or direct light to analyze the cell, the member comprising a starting portion, an end portion configured for insertion into the cell while maintaining viability of the cell, and a tapered portion connecting the starting portion to the end portion, wherein (i) the starting portion has a substantially constant average cross-sectional diameter of at least about 100 micrometers and is configured for guiding the end portion into the cell, (ii) the end portion for insertion into the cell while maintaining viability of the cell has a substantially constant average cross-sectional diameter of less than 100 nm and a length of between about 750 micrometers and about 3 mm, and (iii) the tapered portion connecting the starting portion to the end portion has a length of no more than about 500 micrometers; and
   at least one particle attached to the end portion of the member and configured to facilitate analysis of the cell by interacting with an analyte from the cell such that a characteristic of the analyte is determined by light propagated through the member, wherein (i) the at least one particle is positioned in an optically interrogatable position with respect to light transmitted through the member to the end portion, (ii) the at least one particle is attached to the end portion of the member via an adhesive positioned between the at least one particle and the end portion of the member, and (iii) the adhesive comprises at least one of a polymer or an epoxy, wherein the member is formed by etching.

2. The article of claim 1, wherein the member comprises a metal.

3. The article of claim 1, wherein the member comprises glass.

4. The article of claim 1, wherein the member is able to transmit light.

5. The article of claim 1, wherein the at least one particle comprises a metal.

6. The article of claim 1, wherein the at least one particle is at least partially coated with a reaction entity.

7. The article of claim 1, wherein the end portion of the member is coated with a plurality of particles.

8. The article of claim 1, wherein the end portion is at least partially inserted into the cell.

9. The article of claim 1, wherein the at least one particle is in surface plasmon resonance (SPR) communication with the member.

10. The article of claim 5, wherein the at least one particle comprises gold.

11. The article of claim 5, wherein the at least one particle comprises silver.

12. The article of claim 5, wherein the at least one particle comprises aluminum.

13. The article of claim 1, wherein the at least one particle comprises a polymer, silica or glass.

14. The article of claim 1, wherein the member comprises gold.

15. The article of claim 1, wherein the member comprises silicon.

16. The article of claim 6, wherein the reaction entity comprises a binding partner to which the analyte binds.

17. The article of claim 6, wherein the reaction entity comprises a metal, a nucleic acid, an antibody, an aptamer, a sugar, a carbohydrate, a protein, a polymer, a catalyst, and/or a quantum dot.

18. The article of claim 6, wherein the reaction entity comprises platinum.

19. The article of claim 6, wherein the reaction entity comprises a hydrogel.

20. The article of claim 1, wherein facilitating analysis of the cell comprises determining a vibration characteristic and/or a change in the vibration characteristic of the member.

21. The article of claim 20, wherein the vibration characteristic and/or the change in the vibration characteristic of the member is due to a change in temperature, electric field, and/or magnetic field of the cell.

22. The article of claim 1, wherein the adhesive comprises the polymer.

23. The article of claim 1, wherein the adhesive is the epoxy.

24. The article of claim 1, wherein the cell is a HeLa cell.

25. The article of claim 1, wherein the member is configured to guide and/or direct light applied to the starting portion and directed to the cell via the tapered portion and the end portion.

* * * * *